United States Patent
Cohen et al.

(10) Patent No.: US 11,291,670 B2
(45) Date of Patent: Apr. 5, 2022

(54) THERAPEUTIC APPROACHES FOR TREATING ALZHEIMER DISEASE AND RELATED DISORDERS THROUGH A MODULATION OF ANGIOGENESIS

(75) Inventors: Daniel Cohen, Le Vesinet (FR); Ilya Chumakov, Vaux le Penil (FR); Serguei Nabirochkin, Chatenay Malabry (FR); Oxana Guerassimenko, Milly-la-Foret (RU); Esther Graudens, Paris (FR)

(73) Assignee: PHARNEXT, Paris (FR)

( * ) Notice: Subject to any disclaimer, the term of this patent is extended or adjusted under 35 U.S.C. 154(b) by 0 days.

(21) Appl. No.: 12/915,709

(22) Filed: Oct. 29, 2010
(Under 37 CFR 1.47)

(65) Prior Publication Data
US 2012/0058992 A1 Mar. 8, 2012

Related U.S. Application Data

(63) Continuation-in-part of application No. PCT/EP2009/055205, filed on Apr. 29, 2009.

(60) Provisional application No. 61/048,583, filed on Apr. 29, 2008.

(30) Foreign Application Priority Data

Apr. 29, 2009 (WO) .............. PCT/EP2009/055205

(51) Int. Cl.
| | | |
|---|---|---|
| A61K 31/55 | (2006.01) | |
| A61K 31/42 | (2006.01) | |
| A61K 31/37 | (2006.01) | |
| A61K 31/4365 | (2006.01) | |
| A61K 45/06 | (2006.01) | |
| A61K 31/155 | (2006.01) | |
| A61K 31/195 | (2006.01) | |
| A61K 31/64 | (2006.01) | |

(52) U.S. Cl.
CPC .......... *A61K 31/55* (2013.01); *A61K 31/155* (2013.01); *A61K 31/195* (2013.01); *A61K 31/37* (2013.01); *A61K 31/42* (2013.01); *A61K 31/4365* (2013.01); *A61K 31/64* (2013.01); *A61K 45/06* (2013.01)

(58) Field of Classification Search
USPC ................................................ 514/214.02
See application file for complete search history.

(56) References Cited

U.S. PATENT DOCUMENTS 5,556,870 A * 9/1996 Weithmann et al. ......... 514/378

FOREIGN PATENT DOCUMENTS

WO WO 03/061767 7/2003

OTHER PUBLICATIONS

Levin (Baclofen interactions with nicotine in rats: effects on memory, Pharmacology, Biochemistry and Behavior 79 (2004) pp. 343-348).*
Wolff, Manfred E. "Burger's Medicinal Chemistry, 5ed, Part I", John Wiley & Sons, 1995, pp. 975-977.*
Bromley (Churchill Livingstone, 2006, pp. 1-3).*
Chu (Quantitative autoradiography of hippocampal GABAB and GABAA receptor changes in Alzheimer's disease, Neuroscience Letters, 82, 1987, pp. 246-252.*
Finnimore (The effects of the GABA agonist, baclofen, on sleep and breathing, Eur Respir J, 1995, 8, pp. 230-234).*
Ciccaglione (Effect of acute and chronic administration of the GABAB agonist baclofen on 24 hour pH metry and symptoms in control subject and in patients with gastro-esophageal reflux disease, Gut, 2003, 52, pp. 464-470).*
Crystal (Baclofen Theram Mav Be Associated witg Choria in Alzheimer's Disease, the American Neurological Association, Dec. 1990, p. 1).*
Crystal, H.A., "Baclofen therapy may be associated with chorea in Alzheimer's disease," Annals Neurology, vol. 28, No. 6, p. 839 (1990) XP9024224.
Lee et al., "Phenformin suppresses calcium responses to glutamate and protects hippocampal neurons against excitotoxicity," Experimental Neurology, vol. 175, No. 1, pp. 161-167 (2002) XP002538106.
Delagarza et al., "Pharmacologic Treatment of Alzheimer's Disease: An Update," American Family Physician, vol. 68, No. 7, pp. 1365-1372 (2003), XP008091098.
Vagnucci et al., "Alzheimer's disease and angiogenesis," The Lancet, vol. 361, No. 9357, pp. 605-608 (2003) XP004778573.
International Search Report, PCT Application No. PCT/EP2009/055205, dated Nov. 16, 2009 (2 pages).
Bowery, "GABA$_B$ receptor: a site of therapeutic benefit", Current Opinion in Pharmacology 2006, 6:37-43.
Bullock, "SGS-742 Novartis", Current Opinion in Investigational Drugs 2005 6(1):108-113.
Froestle, et al., "SGS742: the first GABA$_B$ receptor antagonist in clinical trials", Biochemical Pharmacology 68 (2004) 1479-1487.
Heese, et al., "GABA$_B$ receptor antagonists elevate both mRNA and protein levels of the neurotrophins nerve growth factor (NGF) and brain-derived neurotrophic factor (BDNF) but not neurotrohin-3 (NT-3) in brain and spinal cord of rats", Neuropharmacology 39 (2000) 449-462.
Lafon-Cazal, et al., "mGluR7-like receptor and GABA$_B$ receptor activation enhance neurotoxic effects of N-methyl-$_D$-aspartate in cultured mouse striatal GABAergic neurones", Neuropharmacology 38 (1999) 1631-1640.

(Continued)

*Primary Examiner* — Kathrien A Cruz
(74) *Attorney, Agent, or Firm* — Browdy and Neimark, PLLC

(57) ABSTRACT

The present invention relates to compositions and methods for the treatment of Alzheimer's disease and related disorders. More particularly, the invention relates to combined therapies that modulate angiogenesis for treating said disease.

12 Claims, 6 Drawing Sheets

(56) References Cited

OTHER PUBLICATIONS

Lehmann, et al., "Effects of Repeated Administration of Baclofen to Rats on GABA$_B$ Receptor Binding Sites and Subunit Expression in the Brain", Neurochemical Research, vol. 28, No. 2, Feb. 2003, pp. 387-393.

Maubach, "GABA$_A$ Receptor Subtype Selective Cognition Enhancers", Current Drug Targets—CNS & Neurological Disorders, 2003, 2, 233-239.

Pratt, et al., "Repeated administration of desipramine and a GABA$_B$ receptor antagonist, CGP 36742, discretely up-regulates GABA$_B$ receptor binding sites in rat frontal cortex", Br. J. Pharmacol. (1993), 110, 724-735.

Yoshiike, et al., "GABA$_A$ Receptor-Mediated Acceleration of Aging-Associated Memory Decline in APP/PS1 Mice and Its Pharmacological Treatment by Picrotoxin", PLoS ONE 3(8):e3029 (2008).

Canas et al., Predominant loss of glutamatergic terminal markers in a β-amyloid peptide model of Alzheimer's disease, Neuropharmacology, 76 Pt A:51-56, (2014) Abstract.

Genkova-Papazova et al., The GABA-B antagonist CGP 36742 prevents PTZ-kindling-provoked amnesia in rats, Eur. Neuropsychopharmacol., 10(4):273-278 (2000) Abstract.

Greenamyre et al., Dementia of the Alzheimer's type: changes in Hippocampal L[3-H] glutamate binding. J. Neurochem., 48(2):543-551 (1987).

Iwakiri et al., An immune-histochemical study of GABAA receptor gamma subunits in Alzheimer's disease hippocampus: relationship to neurofibrillary tangle progression, Neuropathology, 29(3):263-269 (2009).

Lee et al., Chronic stimulation of GABAA receptor with muscimol reduces amyloid beta protein (25-35)-induced neurotoxicity in cultured rat cortical cells, Neurosci.Res., 52(4):347-56 (2005) Abstract.

Marcade et al., Etazolate, a neuroprotective drug linking GABA(A) receptor pharmacology to amyloid precursor protein processing, J. Neurochem., 106(1):392-404 (2008) Abstract.

Meyer et al., Positron emission tomography measures of benzodiazepine binding in Alzheimer's disease, Arch. Neural., 52(3):314-7 (1995) Abstract.

Mitew et al., Neurites containing the neurofilament-triplet proteins are selectively vulnerable to cytoskeletal pathology in Alzheimer's disease and transgenic mouse models, Front Neuroanat., 7(30):1-10 (2013).

Mondadori et al., CGP 36742: the first orally active GABAB blocker improves the cognitive performance of mice, rats, and rhesus monkeys, Behav Neural Biol., 60(1):62-68 (1993) Abstract.

Reinikainen et al., A post-mortem study of noradrenergic, serotonergic and GABAergic neurons in Alzheimer's disease, J Neural Sci., 84(1):101-116 (1988) Abstract.

Rissman et al., Biochemical analysis of GABAA receptor subunits aalpha 1, alpha 5, beta 1, beta 2 in the hippocampus of patients with Alzheimer's disease neuropathology, Neuroscience, 120(3):695-704 (2003) Abstract.

Vogt et al., Laminar Alterations in gamma-aminobutyric Acid A muscarinic, and beta adrenoceptors and neuron degeneration in the cingulate cortex in Alzheimer's Disease, J Neurochem., 57(1):282-290 (1991) Abstract.

* cited by examiner

THERAPEUTIC APPROACHES FOR TREATING ALZHEIMER DISEASE AND RELATED DISORDERS THROUGH A MODULATION OF ANGIOGENESIS

CROSS REFERENCE TO RELATED APPLICATION

This application is a continuation-in-part of PCT Application No. PCT/EP2009/055205, filed on Apr. 29, 2009, which is a non-provisional of U.S. Provisional Application No. 61/048,583, filed on Apr. 29, 2008, the contents of both of the foregoing applications are hereby incorporated by reference in their entirety.

BACKGROUND OF THE INVENTION

The present invention relates to compositions and methods for the treatment of Alzheimer's disease (AD) and related disorders.

AD is the prototypic cortical dementia characterized by memory deficit together with dysphasia (language disorder in which there is an impairment of speech and of comprehension of speech), dyspraxia (disability to coordinate and perform certain purposeful movements and gestures in the absence of motor or sensory impairments) and agnosia (ability to recognize objects, persons, sounds, shapes, or smells) attributable to involvement of the cortical association areas. Special symptoms such as spastic paraparesis (weakness affecting the lower extremities) can also be involved (1-4).

Incidence of Alzheimer disease increases dramatically with the age. AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis (5).

The incidence rate of AD increases dramatically with age. United Nation population projections estimate that the number of people older than 80 years will approach 370 million by the year 2050. Currently, it is estimated that 50% of people older than age 85 years are afflicted with AD. Therefore, more than 100 million people worldwide will suffer from dementia in 50 years. The vast number of people requiring constant care and other services will severely affect medical, monetary and human resources (6).

Memory impairment is the early feature of the disease and involves episodic memory (memory for day-today events). Semantic memory (memory for verbal and visual meaning) is involved later in the disease. By contrast, working memory (short-term memory involving structures and processes used for temporarily storing and manipulating information) and procedural memory (unconscious memory that is long-term memory of skills and procedure) are preserved until late. As the disease progresses, the additional features of language impairment, visual perceptual and spatial deficits, agnosias and apraxias emerge.

The classic picture of Alzheimer's disease is sufficiently characteristic to allow identification in approximately 80% of cases (7). Nevertheless, clinical heterogeneity does occur and not only is this important for clinical management but provides further implication of specific medication treatments for functionally different forms. (8).

The pathological hallmark of AD includes amyloid plaques containing beta-amyloid (Abeta), neurofibrillary tangles (NFT) containing Tau and neuronal and synaptic dysfunction and loss (9-11). For the last decade, two major hypotheses on the cause of AD have been proposed: the "amyloid cascade hypothesis", which states that the neurodegenerative process is a series of events triggered by the abnormal processing of the Amyloid Precursor Protein (APP) (12), and the "neuronal cytoskeletal degeneration hypothesis" (13), which proposes that cytoskeletal changes are the triggering events. The most widely accepted theory explaining AD progression remains the amyloid cascade hypothesis (14-16) and AD researchers have mainly focused on determining the mechanisms underlying the toxicity associated with Abeta proteins. On contrary, Tau protein has received much less attention from the pharmaceutical industry than amyloid, because of both fundamental and practical concerns. Moreover, synaptic density change is the pathological lesion that best correlates with cognitive impairment than the two others. Studies have revealed that the amyloid pathology appears to progress in a neurotransmitter-specific manner where the cholinergic terminals appear most vulnerable, followed by the glutamatergic terminals and finally by the GABAergic terminals (11).

SUMMARY OF INVENTION

The purpose of the present invention is to provide new therapeutic approaches for treating AD and related disorders.

The inventors have identified a molecular pathway which is involved in the genesis of AD and offers novel targets for development of new treatments to ameliorate AD and related disorders, particularly for the development of combination therapies using novel or existing molecules previously used in other indications. More particularly, the inventors have identified several drugs which, alone or in combination(s), can effectively affect such pathway and represent a new and effective therapy for the treatment of AD and related disorders.

The invention therefore provides novel compositions and methods for treating AD disease and related disorders.

More particularly, the invention relates to compositions suitable for treating Alzheimer's disease or a related disorder in a subject in need thereof, wherein said compositions comprise a drug that increases angiogenesis.

A further object of this invention relates to compositions suitable for treating Alzheimer's disease or a related disorder in a subject in need thereof, wherein said compositions comprise a combination of at least two drugs that increase angiogenesis, for combined, separate or sequential administration.

More preferably, the drug or drugs that increase angiogenesis bind to or modulate the activity of a protein encoded by a gene selected from ABCA1, ACAT, ACC2, ADAMTS12, ADCY2, ADIPOQ, ADIPOR1, ADIPOR2, ADRB2, AGPAT5, AIP4, AKAP2, AKR1C2, AMPK, ANG2, ANK1, ANXA1, APOA1, ARHGAP17, ATP10A, AUH, AUTOTAXIN, BA13, BCAR1, BIN1, BMP3A, CA10, CAMK1D, CAMKK2, CD36, CD44, CDC42, CDH13, CHAT, CNTFR, COL4A2, CPT, CSH1, CTNN, CUBN, CYP7B1, CYSLTR1, CYSLTR2, DGKB, DGKH, DGKZ, DHCR7, DHFR, DRD2, DRD5, EDG1, EDG2, EDG3, EDG4, EDG5, EDG6, EDG7, EDG8, EDNRA, EHHADH, ENPP6, ERBB4, ERK1, ERK2, ESRRG, ETFA, F2, FDPS, FGF2, FLNA, FLT4, FOXO1, FOXO3A, FTO, GABBR2, GATA3, GH1, GNA12, GNA13, GRK2, GRK5, GRM5, HAPLN1, HAS1, HAS2, HAS3, HCRTR2, HIF1A, HSD11B1, HYAL1, HYAL2, HYAL3, IL20RA, IL20RB, IL6ST, IL8, ITGA6, ITGB1, KDR, LAMA1, LDLR, LEPR, LEPTIN, LIFR, LIPL2, LKB1, LRP, LTBP2, MAT2B, ME1 MEGALIN, MERLIN, MET, MGST2, MMP2, MMP9, MTOR, MTR, NCK2, NEDD9, NFKB1, NFKBIB, NOS2A, NOS3, NR1I2, NR3C2, NRG1, NRP1, NRP2, OPRS1, OSBPL10, OSBPL3, OSTEOPONTIN, P2RY1, P2RY12, PAI1, PAI2, PAK1, PAK6, PALLD, PAP1, PAR1, PAXILLIN, PC, PCTP, PDE11A, PDE1A, PDE3A, PDE4D, PDE5, PDGFA, PDGFB, PDGFRA, PDGFRB, P13K, PITPNC1, PKA, PKCD, PLA1A, PLA2, PLAT, PLAU, PLCB1, PLD1, PLD2, PLG, PLXDC2, PPARA, PPARG, PPARGC1B, PRKG1, PRL, PTGS2, PTN, PTPN11, PYK2, RAC1, RAS, RHEB, RHOA, ROCK1, ROCK2, RPS6KA1, RPS6 KB2, SCARB1, SCHIP1, SGPP2, SLC25A21, SMAD3, SMAD4, SNCA, SORBS2, SPLA2, SPOCK1, SRD5A1, SREBF1, SREBF2, STAT3, TGFBR1, TGFBR2, TGFBR3, THBS1, THBS2, THEM2, THRB, TIAM1, TIMP2, TLL2, TSC1, TSC2, TSPO, VEGFA, VEGFR1, and YES1.

Specific and preferred examples of such drugs include, without limitation, compounds selected from acamprosate, albuterol, alendronate, ambrisentan, aminocaproic acid, argatroban, baclofen, balsalazide, becaplermin, cabergoline, cilostazol, clopidogrel, desirudin, dihydroergotamine, eplerenone, fenoldopam, fludrocortisone, flunitrazepam, gemfibrozil, hesperetin, imatinib, ketotifen, leflunomide, levosimendan, L-histidine, liothyronine, marimastat, meloxicam, mepacrine, methazolamide, methimazole, milrinone, montelukast, netilmicin, nitroglycerin, nitroprusside, pegaptanib, pentazocine, phenformin, sodium phenylbutyrate, pyrimethamine, sulfisoxazole, sunitinib, tadalafil, temazepam, terbinafine, thiethylperazine, tirofiban, topiramate, topotecan, vidarabine and warfarin, or a combination thereof.

In a particular embodiment, the compositions of this invention further comprise at least one drug that modulates synapse function, for combined, separate or sequential use.

Alternatively, or in addition, the compositions of this invention may further comprise at least one drug that modulates cell stress response, for combined, separate or sequential use.

The compositions of this invention typically further comprise a pharmaceutically acceptable carrier or excipient.

A further object of this invention resides in a method of producing a drug for treating Alzheimer's disease or a related disorder, the method comprising a step of testing a candidate drug for activity on angiogenesis and selecting candidate drugs that increase angiogenesis.

The invention also relates to a method of producing a composition for treating Alzheimer's disease or a related disorder, the method comprising preparing a combination of a drug that increases angiogenesis and a drug that modulates synapse function or cell stress response, and formulating said combination of drugs for simultaneous, separate or sequential administration thereof to a subject in need thereof.

The invention further relates to a method of treating Alzheimer's disease or a related disorder, the method comprising simultaneously, separately or sequentially administering to a subject in need thereof a drug or a combination of drugs that increase angiogenesis.

The invention further relates to a method of treating Alzheimer's disease or a related disorder, the method comprising simultaneously, separately or sequentially administering to a subject in need thereof a drug that increase angiogenesis and a drug that modulates synapse function and/or a drug that modulates cell stress response.

The invention further relates to the use of a drug that increases angiogenesis for the manufacture of a medicament for treating Alzheimer's disease or a related disorder.

The invention further relates to the use of a combination of at least two drugs that increase angiogenesis for the manufacture of a medicament for treating Alzheimer's disease or a related disorder, wherein said at least two drugs are administered together, separately or sequentially.

As discussed in the present application, the above therapies and combination therapies provide novel and effective approaches for treating AD in human subjects.

ANOVA+Bunett Post-Hoc test. The human amyloid peptide (Aβ$_{1-42}$ 2.5 μM) produces a significant intoxication, above 40%, compared to vehicle-treated neurons. This intoxication is significantly prevented by the combination of Baclofen and Levosimendan whereas, at these concentrations, Levosimendan and Baclofen, alone, have no significant effect on intoxication.

Figure 6:
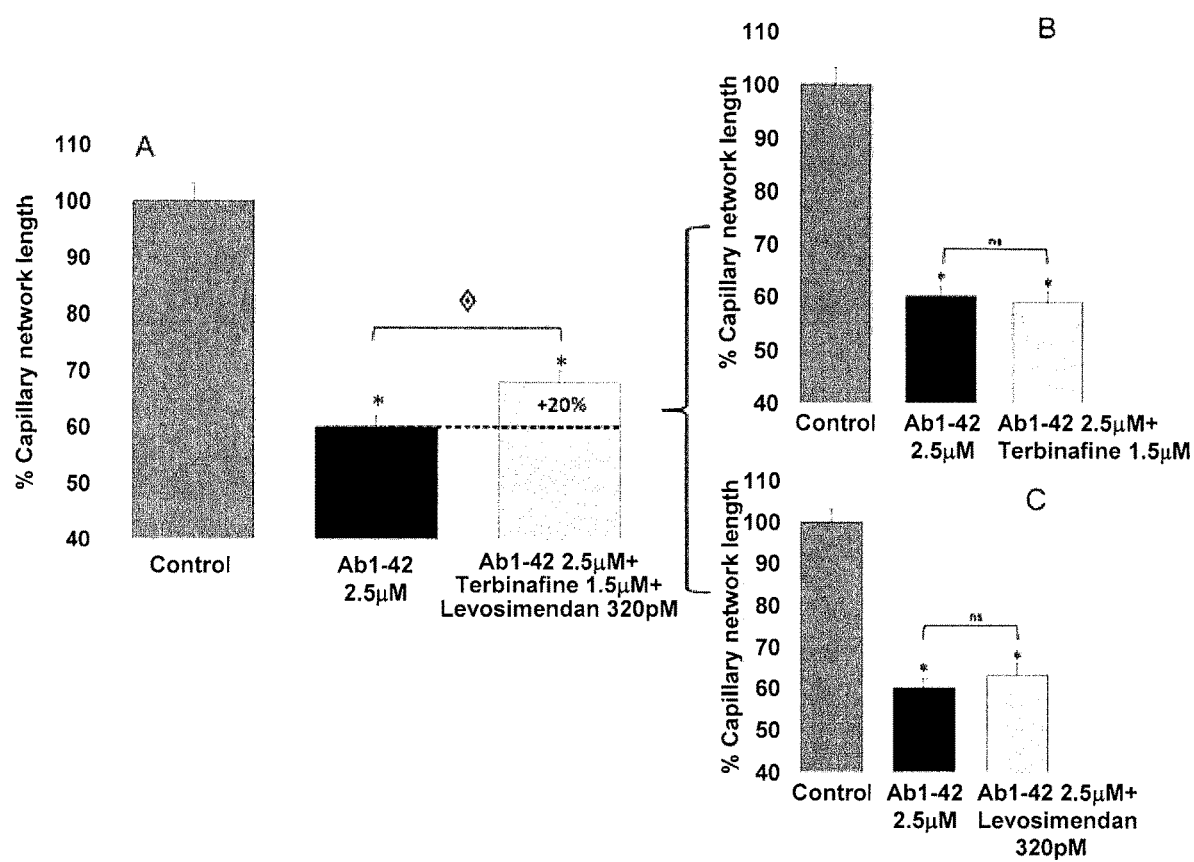

FIG. 6: Effect of a selected combination therapy on the total length of capillary network in beta-amyloid intoxicated HBMEC cultures. ◊: p<0.05, significantly different from Aβ$_{1-42}$. *: p<0.05, significantly different from vehicle. ANOVA+Bunett Post-Hoc test. The human amyloid peptide (Aβ$_{1-42}$ 2.5 μM) produces a significant intoxication, above 40%, compared to vehicle-treated neurons. This intoxication is significantly prevented by the combination of Terbinafine and Levosimendan whereas, at these concentrations, Levosimendan and Terbinafine alone have no significant effect on intoxication.

DETAILED DESCRIPTION OF THE INVENTION

The present invention provides new therapeutic approaches for treating AD or related disorders. The invention discloses novel use of drugs or drug combinations which allow an effective correction of such diseases and may be used for patient treatment.

The term "AD related disorder" designates Alzheimer's disease (AD), senile dementia of AD type (SDAT), Parkinson's disease, Lewis body dementia, vascular dementia, mild cognitive impairment (MC1), age-associated memory impairment (AAMI) and problem associated with ageing, post-encephalitic Parkinsonism, ALS and Down syndrome.

As used herein, "treatment" of a disorder includes the therapy, prevention, prophylaxis, retardation or reduction of symptoms provoked by the disorder. The term treatment includes in particular the control of disease progression and associated symptoms.

The term "increase", as it refers to angiogenesis, includes any increase in the angiogenesis as compared to the existing level in the subject. Such amelioration may include a restoration, i.e., to normal levels, or lower increase, which are still sufficient to improve the patient condition. Such an increase can be evaluated or verified using known biological tests, such as described in the experimental section. Also, the designation of specific compounds within the context of this invention is meant to include not only the specifically named molecules, but also any pharmaceutically acceptable salt, hydrate, ester, ether, isomers, racemate, conjugates, or pro-drugs thereof.

The term "combination" designates a treatment wherein at least two or more drugs are co-administered to a subject to cause a biological effect. In a combined therapy according to this invention, the at least two drugs may be administered together or separately, at the same time or sequentially. Also, the at least two drugs may be administered through different routes and protocols. As a result, although they may be formulated together, the drugs of a combination may also be formulated separately.

As discussed above, the invention relates to compositions and methods for treating Alzheimer's disease or a related disorder in a subject in need thereof, using a drug or a combination of drugs that increases angiogenesis.

By a comprehensive integration of experimental data covering results of cell biology studies, expression profiling experiments and genetic association studies, describing different aspects of Alzheimer's disease and links existing in cellular signalling and functional pathways, the inventors have uncovered that angiogenesis represents a important mechanism which is altered in subjects having AD. Genes located in said functional network and implicated in Alzheimer's disease were selected by the following criteria:

(1)—direct interaction with the genes causatively responsible for familial cases of Alzheimer's disease (APP, ApoE, presenilins, tau protein),
(2)—functional partners of the genes selected by the criterion (1),
(3)—nearest functional partners of the genes selected by the criterion (2).

Through this process, the inventors were able to establish that the network responsible for angiogenesis is a major functional network affected in Alzheimer's disease.

Angiogenesis plays a fundamental role in ensuring a tissue homeostasis and in adaptive responses to environmental and physiological challenges such as hypoxia or wound healing; its dysfunction contributes to the pathogenesis of numerous and heterogeneous pathologies varying from cardiovascular complications to tumour's growth and metastasis.

Although Alzheimer's disease is traditionally considered as a neurodegenerative condition accompanied by collateral vascular pathology, our analysis allow re-evaluation of the pathogenic impact of the vascular deregulation and attribute an important and probably causative role to angiogenic pathways in aetiology of this disease. We found that genes regulating angiogenesis are extremely enriched in signalling networks implicated in Alzheimer's disease. This conclusion has deep consequences for prevention and curing of Alzheimer disease and provides new guidelines for combinatorial treatment of this complex neurodegenerative disorder. We also found that this network could be formally subdivided into the families of angiogenic factors and of proteins from the two pathways (AMPK pathway and LPA metabolic pathway) tightly involved in regulation of angiogenesis.

Amyloid Abeta protein affects strongly not only the biology of neurons, but possesses also a strong anti-angiogenic activity (17). Another gene, causatively associated with familial cases of Alzheimer disease—presinilin is able to modulate—by means of regulation of intramembrane proteolysis—angiogenesis through several independent signalling pathways mediated by its functional substrates VEGFR1, ErbB4, Notch, DCC, CD44, ephrin receptors and cadherins (18-20).

Gene CD44 encodes a receptor for hyaluronic acid (HA), whose degradation products promote angiogenesis (21). This receptor was implicated in the organization and/or stabilization of the endothelia of forming or newly formed vessels (22). It can also bind and regulates activity of proteins such as osteopontin, collagens, and matrix metalloproteinases (MMPs) implicated in extracellular matrix dynamic, which accompanies formation of new blood vessels (23).

Other membrane receptors identified by our data mining include IL20Rα, LEPTR, NRP1 and NRP2, and endothelin EDNRA receptor. IL20Rα gene encodes a receptor for IL20, a pleiotropic cytokine involved in vascular tube formation (24). Leptin, an endocrine hormone and ligand for LEPTR, stimulates angiogenesis synergistically with fibroblast growth factor FGF-2 and vascular endothelial growth factor (VEGF), the two most potent and ubiquitously expressed angiogenic factors. As well, it is involved in the increase of vascular permeability (25). NRP1 and NRP2 are transmembrane co-receptors modulating VEGFR-2 signalling activation, which assures developmental angiogenesis (26).

Finally, we also selected a group of genes involved in organization and remodelling of extracellular matrix (THBS2, LAMA1, COL4A2, ADAMTS12 and ADAM10) or in functional processing (TLL2) of well-known angiogenic modulators such as prolactin, growth hormone, and placental lactogen (27).

The AMP-activated protein kinase (AMPK) family is recognized as an intracellular sensor of AMP: ATP ratio and plays a major role in maintaining energy homeostasis by regulating metabolic processes, such as glucose or fatty acid metabolism. This family of serine/threonine kinases is activated by metabolic stresses that inhibit ATP production or stimulate ATP consumption (28).

In addition to its well established role in control of cell energy balance, AMPK signalling is also a regulator of angiogenesis required for endothelial cell migration and differentiation under conditions of hypoxia (29). This kinase is one of the downstream effectors responsible for pro-angiogenic effects of VEGF (30), adiponectin (31), IGF-1 and, probably, PPARγ receptor. AMPK is found to be abnormally activated in double-transgenic APP/PS2 mice, an in vivo model of Alzheimer disease (32).

We have identified several genes associated with Alzheimer disease and representing both upstream modulators and down-stream effectors of the AMP-activated kinases. Among upstream modulators of the AMPK proteins, leptin and CNTF receptors, CDH13 (33), a putative co-receptor for adiponectin Acrp30, and trombin signalling pathways could be mentioned, as well as CAMKK2β kinase that—together with the LKB1 kinase—is recognized as a main direct modulator of AMPK activity (28).

Regarding downstream effectors of AMPK, genes involved in fatty acids and cholesterol metabolism represent particular interest. Notably, ACC2 gene, well established target of the AMPK signaling, encodes the Acetyl-CoA carboxylase (ACC) that catalyzes the ATP-dependent carboxylation of Acetyl-CoA to Malonyl-CoA, and thus controls the rate-limiting step in fatty acid synthesis. Activated AMPK phosphorylates ACC2 protein, decreases its enzymatic activity and therefore enhances fatty acid oxidation. Several other, mainly mitochondrial, genes involved in fatty acids metabolism, such as EFTA, AUH, SLC25A21, PC, ME1 and EHHADH could also participate in AMPK-mediated control of cellular energy balance in context of Alzheimer's disease. Among them, PC gene encodes pyruvate carboxylase and is involved in multiple metabolic pathways, such as gluconeogenesis, lipogenesis and synthesis of the neurotransmitter glutamate. It has been shown that impairment in PC activity could be related to brain dysfunction (34-35). Interestingly, the GABA(B) receptor was also identified as a functional target for AMP-activated kinase. A recent study demonstrated that AMPK activation could be neuroprotective—via phosphorylation of the GABA(B) receptor (36)—and thus might participate in progression of the amyloid pathology targeting GABAergic terminals (11).

Further, the AMPK signalling pathway could modify evolution of Alzheimer's disease-associated lesions by influencing cholesterol metabolism. AMPK can influence cholesterol metabolism by reducing activity of SREBP transcription factors (37).

SREBP proteins are main sensors and regulators of intracellular cholesterol levels; being activated by proteolytic cleavage when cholesterol level falls, SREBPs bind to specific sterol regulatory element (SRE) in promoter regions of genes encoding enzymes, involved in cholesterol biosynthesis, and enhance their transcription.

Cholesterol not only serves as a precursor for biosynthesis of neuroprotective steroids, but is also recognized as an important regulator of membrane fluidity and plays a pivotal role in dynamics of lipid rafts, concentrating platforms for a variety of molecules involved in membrane sorting, trafficking and signal transduction. Intermediate products in cholesterol biosynthesis generated by farnesyl-PP and geranygeranyl-PP synthases play a pivotal role in modulating activity of small GTPases, including RhoA and Rac, which are major regulators of angiogenesis and axon growth.

Several other genes implicated in cholesterol metabolism and transport could also influence development of Alzheimer's disease. DHCR7, SRD5A1 and CYP7B1 proteins are involved in production of steroids that could protect neuronal cells against toxic insults associated with Alzheimer's disease (38). ABCA1 gene that encodes a member of the ATP-binding cassette (ABC) transporter family also represents a particular interest, as it controls secretion of ApoE lipoprotein, the main predisposition risk factor for development of Alzheimer's disease (39).

Phosphatidic acid (PA), lysophosphatidic acid (LPA), and sphingosine 1-phosphate (S1P) are natural phospholipids that possess potent signaling properties. Notably, these phospholipid growth factors display divergent effects on angiogenic potential of endothelial cells and could—in complementary, combined manner—effectively induce neovascularization. S1P is mainly involved in promotion of chemotactic migration of endothelial cells, while LPA is more implicated in stabilization of endothelial monolayer barrier function at late stages in angiogenesis (40).

LPA affects angiogenesis either by modulating activity of RhoA GTPase or by enhancing expression of several angiogenic factors—VEGF, PDGFB and IL-8 (41-45). Besides its tight involvement in angiogenesis, LPA is also recognized as an extracellular lipid signaling provoking neurite growth cone collapse and influencing migration of early postmitotic neurons during development (46).

LPA can be synthesized by a secreted lysophospholipase D (autotaxin) and acts via specific G protein-coupled EDG2, EDG4 and EDG7 receptors affecting cell proliferation, survival and motility (47). Most likely, the ability of LPA to control cellular morphology and motility is mediated by activation of RhoA-ROCK signalling module through the $G_{12/13}$ protein (48).

Some experimental data indicate an important role for LPA-mediating signalling in pathogenesis of Alzheimer's disease. It has been demonstrated that autotaxin expression is enhanced in frontal cortex of Alzheimer-type dementia patients (49), and neurite retraction induced by LPA in vitro is accompanied by increased Alzheimer's disease-like phosphorylation pattern of tau protein in differentiated human neuroblastoma cells (50). Moreover, genetic manipulations with APP or presenilin proteins affect expression of the autotoxin enzyme in brains of the transgenic mice (51-52).

Using our data mining approach, we identified a large number of genes, involved in LPA metabolism or modulated by LPA signaling and potentially linked to progression of Alzheimer's disease (MTR, MAT2B, CUBN, ATP10A, THEM2, PITPNC1, ENPPG, SGPP2, AGPAT, DGKH, DGKB, MGST2, PLD2, and DRD2). Among them, the CUBN gene encodes a receptor for intrinsic factor-vitamin B12, whereas deficiency in folate and cobalamin (Vitamin B9 and B12) bioavailability was previously associated with pathogenesis of Alzheimer's disease (53).

In the present invention, the inventors propose novel compositions, which can be used to increase angiogenesis altered in Alzheimer's disease and other neurogenerative disorders.

In a particular embodiment, the compositions and methods of treating AD according to this invention use drugs that increase angiogenesis through their interaction with or modulation of one gene or protein as listed above.

More specifically, the compositions of this invention comprise a drug or drugs that increase angiogenesis through the binding to or modulation of the activity of a protein encoded by a gene selected from ABCA1, ACAT, ACC2, ADAMTS12, ADCY2, ADIPOQ, ADIPOR1, ADIPOR2, ADRB2, AGPAT5, AIP4, AKAP2, AKR1C2, AMPK, ANG2, ANK1, ANXA1, APOA 1, ARHGAP17, ATP10A, AUH, AUTOTAXIN, BAI3, BCAR1, BIN1, BMP3A, CA10, CAMK1D, CAMKK2, CD36, CD44, CDC42, CDH13, CHAT, CNTFR, COL4A2, CPT, CSH1, CTNN, CUBN, CYP7B1, CYSLTR1, CYSLTR2, DGKB, DGKH, DGKZ, DHCR7, DHFR, DRD2, DRD5, EDG1, EDG2, EDG3, EDG4, EDG5, EDG6, EDG7, EDG8, EDNRA, EHHADH, ENPP6, ERBB4, ERK1, ERK2, ESRRG, ETFA, F2, FDPS, FGF2, FLNA, FLT4, FOXO1, FOXO3A, FTO, GABBR2, GATA3, GH1, GNA12, GNA13, GRK2, GRK5, GRM5, HAPLN1, HAS1, HAS2, HAS3, HCRTR2, HIF1A, HSD11B1, HYAL1, HYAL2, HYAL3, IL20RA, IL20RB, IL6ST, IL8, ITGA6, ITGB1, KDR, LAMA1, LDLR, LEPR, LEPTIN, LIFR, LIPL2, LKB1, LRP, LTBP2, MAT2B, ME1 MEGALIN, MERLIN, MET, MGST2, MMP2, MMP9, MTOR, MTR, NCK2, NEDD9, NFKB1, NFKBIB, NOS2A, NOS3, NR1I2, NR3C2, NRG1, NRP1, NRP2, OPRS1, OSBPL10, OSBPL3, OSTEOPONTIN, P2RY1, P2RY12, PAI1, PAI2, PAK1, PAK6, PALLD, PAP1, PAR1, PAXILLIN, PC, PCTP, PDE11A, PDE1A, PDE3A, PDE4D, PDE5, PDGFA, PDGFB, PDGFRA, PDGFRB, PI3K, PITPNC1, PKA, PKCD, PLA1A, PLA2, PLAT, PLAU, PLCB1, PLD1, PLD2, PLG, PLXDC2, PPARA, PPARG, PPARGC1B, PRKG1, PRL, PTGS2, PTN, PTPN11, PYK2, RAC1, RAS, RHEB, RHOA, ROCK1, ROCK2, RPS6KA1, RPS6 KB2, SCARB1, SCHIP1, SGPP2, SLC25A21, SMAD3, SMAD4, SNCA, SORBS2, SPLA2, SPOCK1, SRD5A1, SREBF1, SREBF2, STAT3, TGFBR1, TGFBR2, TGFBR3, THBS1, THBS2, THEM2, THRB, TIAM1, TIMP2, TLL2, TSC1, TSC2, TSPO, VEGFA, VEGFR1, and YES1.

The sequences of all of the above listed genes and proteins are available from gene libraries and can be isolated by techniques known in the art. Furthermore, the activity of these genes and proteins can be assessed by techniques known per se in the art, as discussed in the experimental section.

The invention further describes drugs that can be used to modulate these target genes and proteins. The invention discloses the identification and activity of particular drugs which, either alone but preferentially in combination(s), modulate the above pathway and may be used to treat said diseases. In particular, we identified small molecules which already exist in the literature but being used to treat distinct diseases in human subjects.

In this respect, in a most preferred embodiment, the compositions of this invention comprise at least an inhibitor of ACAT (preferably, hesperetin), a modulator of ADCY2 (preferably, vidarabine), a modulator of AMPK (preferably selected from phenformin and vidarabine), a modulator of AUTOTAXIN (preferably, L-histidine), an inhibitor of CA10 (preferably, methazolamide), an antagonist of CYSLTR1 and CYSLTR2 (preferably, montelukast), an inhibitor of DHFR (preferably, pyrimethamine), a modulator of DRD2 (preferably selected from dihydroergotamine and cabergoline), an agonist of dopamine receptor DRD5 (preferably, fenoldopam), an antagonist of EDNRA (preferably, sulfisoxazole), a modulator of F2 (preferably, warfarin), an inhibitor of FDPS (preferably, alendronate), a modulator of GABBR2 (preferably selected from baclofen and acamprosate), a modulator of HAS1-3 hyaluronan synthases (preferably, leflunomide), a modulator of HIF1A (preferably selected from topotecan and meloxicam), a modulator of MGST2 (preferably, balsalazide), a modulator of MMP2 and MMP9 (preferably, marimastat), a modulator of NOS2A (preferably selected from gemfibrozil, albuterol and thiethylperazine), a modulator of NOS3 (preferably, ketotifen), an agonist of NR1I2 (preferably, topiramate), a modulator of NR3C2 (preferably selected from eplerenone and fludrocortisone), an agonist of OPRS1 (preferably, pentazocine), a modulator of P2RY1 and P2RY12 (preferably selected from clopidogrel and tirofiban), an inhibitor of trombin receptor PAR1 (preferably, argatroban), an inhibitor of PDE 11A (preferably, tadalafil), an inhibitor of PDE3A (preferably, cilostazol), an inhibitor of PDE4D (preferably, milrinone), a modulator of PDGFRA and PDGFRB (preferably selected from becaplermin and imatinib), an inhibitor of phospholipases PLA1A and PLA2 (preferably selected from netilmicin and mepacrine), a modulator of PLAT (preferably, phenylbutyrate), a modulator of PLD2 (preferably selected from ambrisentan and fenoldopam), a modulator of PLG (preferably, aminocaproic acid), an agonist of PPARA (preferably, gemfibrozil), an agonist of PPARG (preferably, sodium phenylbutyrate), an activator of PRKG1 (preferably selected from nitroprusside, nitroglycerin, tadalafil and cilostazol), a modulator of RHOA (preferably selected from alendronate and terbinafine), a modulator of THRB (preferably selected from liothyronine and methimazole), an inhibitor of TROMBIN (preferably, desirudin), a modulator of TSPO (preferably selected from flunitrazepam and temazepam), and/or an antagonist of VEGFR1 (preferably selected from sunitinib and pegaptanib).

As discussed above, the invention particularly proposes to design combination therapies to address the mechanisms of AD and related disorders. In this respect, examples of most preferred target and drug combinations are disclosed below.

More preferably, the composition of the invention comprises at least one of the following combinations of drugs, for combined, separate or sequential administration:
   a modulator of GABBR2 receptor (preferably, baclofen) and a modulator of RHOA (preferably, terbinafine),
   a modulator of GABBR2 receptor (preferably, baclofen) and an antagonist of EDNRA endothelin receptor (preferably, sulfisoxazole),
   a modulator of GABBR2 receptor (preferably, baclofen) and a modulator of HAS1-3 hyaluronan synthases (preferably, leflunomide),
   a modulator of RHOA (preferably, terbinafine) and an antagonist of EDNRA endothelin receptor (preferably, sulfisoxazole),
   a modulator of RHOA (preferably, terbinafine) and a modulator of HAS1-3 hyaluronan synthases (preferably, leflunomide),
   a modulator of RHOA (preferably, terbinafine) and an agonist of dopamine receptor DRD5 (preferably, fenoldopam),
   a modulator of RHOA (preferably, terbinafine) and an inhibitor of phospholipases PLA1A and PLA2 (preferably, mepacrine),
   a modulator of RHOA (preferably, terbinafine) and a modulator of AMPK (preferably, phenformin), a modulator of RHOA (preferably, terbinafine) and a modulator of purinergic receptors P2RY1 and P2RY12 (preferably, clopidogrel), a modulator of GABBR2 receptor (preferably, baclofen) and a modulator of AMPK (preferably, phenformin), a modulator of GABBR2 receptor (preferably, baclofen) and a modulator of purinergic receptors P2RY1 and P2RY12 (preferably, clopidogrel), an antagonist of EDNRA endothelin receptor (preferably, sulfisoxazole) and a modulator of AMPK (preferably, phenformin), a modulator of HAS1-3 hyaluronan synthases (preferably, leflunomide) and an agonist of dopamine receptor DRD5 (preferably, fenoldopam), or a modulator of HAS1-3 hyaluronan synthases (preferably, leflunomide) and an inhibitor of phospholipases PLA1A and PLA2 (preferably, mepacrine).

Most preferred examples of compositions of this invention comprise a compound selected from acamprosate, albuterol, alendronate, ambrisentan, aminocaproic acid, argatroban, baclofen, balsalazide, becaplermin, cabergoline, cilostazol, clopidogrel, desirudin, dihydroergotamine, eplerenone, fenoldopam, fludrocortisone, flunitrazepam, gemfibrozil, hesperetin, imatinib, ketotifen, leflunomide, L-histidine, liothyronine, marimastat, meloxicam, mepacrine, methazolamide, methimazole, milrinone, montelukast, netilmicin, nitroglycerin, nitroprusside, pegaptanib.pentazocine, phenformin, sodium phenylbutyrate, pyrimethamine, sulfisoxazole, sunitinib, tadalafil, temazepam, terbinafine, thiethylperazine, tirofiban, topiramate, topotecan, vidarabine, levosimendan and warfarin, or a combination thereof.

In a preferred embodiment, the compositions according to the invention comprise at least one compound chosen from the group consisting of leflunomide, sulfisoxazole, terbinafine, baclofen, clopidogrel, fenoldopam, mepacrine and phenformin, or salts or prodrugs or derivatives or sustained release formulations thereof.

Most preferred compositions according to the invention comprise at least baclofen or terbinafine, or a salt, prodrug, derivative, or sustained release formulation thereof, for treating Alzheimer's disease (AD) in a subject in need thereof.

In another preferred embodiment, the compositions according to the invention comprise a combination of at least two compounds chosen from the group consisting of leflunomide, sulfisoxazole, terbinafine, baclofen, clopidogrel, fenoldopam, mepacrine and phenformin, or salts or prodrugs or derivatives or sustained release formulations thereof, for simultaneous, separate or sequential administration.

In another embodiment, the compositions of the invention comprise a combination of at least two compounds chosen from the group consisting of leflunomide, sulfisoxazole, terbinafine, baclofen, clopidogrel, fenoldopam, mepacrine, levosimendan and phenformin, or salts or prodrugs or derivatives or sustained release formulations thereof, wherein said composition increases angiogenesis altered in neurodegenerative disorders selected from the group consisting of Alzheimer's disease (AD), Parkinson's disease (PD), Amyotrophic lateral sclerosis (ALS) and multiple sclerosis (MS). In another preferred embodiment, the compositions of the invention comprise a combination of at least two compounds chosen from the group consisting of leflunomide, sulfisoxazole, terbinafine, baclofen, clopidogrel, fenoldopam, mepacrine, levosimendan and phenformin, or salts or prodrugs or derivatives or sustained release formulations thereof, for treating Alzheimer's disease (AD).

In this regard, the preferred composition for treating Alzheimer's disease comprises baclofen or terbinafine in combination with at least one compound chosen from the group consisting of leflunomide, sulfisoxazole, terbinafine, baclofen, clopidogrel, fenoldopam, mepacrine, levosimendan and phenformin, or salts or prodrugs or derivatives or sustained release formulations thereof.

Preferably, the composition of treating Alzheimer's disease or a related disorder in a subject in need thereof, comprises at least one of the following drug combinations for combined, separate or sequential administration:

baclofen and terbinafine,
baclofen and sulfisoxazole,
baclofen and leflunomide,
terbinafine and sulfisoxazole,
terbinafine and leflunomide,
terbinafine and fenoldopam,
terbinafine and mepacrine,
terbinafine and phenformin,
terbinafine and clopidogrel,
baclofen and phenformin,
baclofen and clopidogrel,
sulfisoxazole and phenformin,
leflunomide and fenoldopam,
terbinafine and levosimendan,
leflunomide and mepacrine, or
baclofen and levosimendan.

Each of the above specific drug combinations represents per se a particular object of the present invention.

In the most preferred embodiment, the composition of the invention comprises a combination of at least two compounds selected from leflunomide, terbinafine, sulfisoxazole and baclofen or salts or prodrugs or derivatives or sustained release formulations thereof, for simultaneous, separate or sequential administration.

In another preferred embodiment, the composition according to the invention comprises one or more compounds selected from leflunomide, terbinafine, sulfisoxazole and baclofen, or salts or prodrugs or derivatives or sustained release formulations thereof, for treating Alzheimer's disease or a related disorder.

Examples of most preferred compositions comprise at least:

baclofen and Levosimendan,
terbinafine and sulfisoxazole, or
terbinafine and levosimendan.

In another embodiment, the composition of the invention further comprises at least one drug that increase angiogenesis, for combined, separate or sequential use.

Preferably, said additional drug that increases angiogenesis is selected from an inhibitor of ACAT (preferably, hesperetin), a modulator of ADCY2 (preferably, vidarabine), a modulator of AMPK (preferably, vidarabine), a modulator of AUTOTAXIN (preferably, L-histidine), an inhibitor of CA10 (preferably, methazolamide), an antagonist of CYSLTR1 and CYSLTR2 (preferably, montelukast), an inhibitor of DHFR (preferably, pyrimethamine), a modulator of DRD2 (preferably selected from dihydroergotamine and cabergoline), a modulator of F2 (preferably, warfarin), an inhibitor of FDPS (preferably, alendronate), a modulator of GABBR2 (preferably, acamprosate), a modulator of HIF1A (preferably selected from topotecan and meloxicam), a modulator of MGST2 (preferably, balsalazide), a modulator of MMP2 and MMP9 (preferably, marimastat), a modulator of NOS2A (preferably selected from gemfibrozil, albuterol and thiethylperazine), a modulator of NOS3 (preferably, ketotifen), an agonist of NR1I2 (preferably, topiramate), a modulator of NR3C2 (preferably selected from eplerenone and fludrocortisone), an agonist of OPRS1 (preferably, pentazocine), a modulator of P2RY1 and P2RY12 (preferably, tirofiban), an inhibitor of trombin receptor PAR1 (preferably, argatroban), an inhibitor of PDE11A (preferably, tadalafil), an inhibitor of PDE3A (preferably, cilostazol), an inhibitor of PDE4D (preferably, milrinone), a modulator of PDGFRA and PDGFRB (preferably selected from becaplermin and imatinib), an inhibitor of PLA1A and PLA2 (preferably, netilmicin), a modulator of PLAT (preferably, sodium phenylbutyrate), a modulator of PLD2 (preferably, ambrisentan), a modulator of PLG (preferably, aminocaproic acid), an agonist of PPARA (preferably, gemfibrozil), an agonist of PPARG (preferably, phenylbutyrate), an activator of PRKG1 (preferably selected from nitroprusside, nitroglycerin, tadalafil and cilostazol), a modulator of RHOA (preferably, alendronate), a modulator of THRB (preferably selected from liothyronine and methimazole), an inhibitor of TROMBIN (preferably, desirudin), a modulator of TSPO (preferably selected from flunitrazepam and temazepam), and/or an antagonist of VEGFR1 (preferably selected from sunitinib and pegaptanib).

In other embodiments, said additional drug that increases angiogenesis is selected from the drug or drugs that bind to or modulate the activity of a protein encoded by a gene selected from ABCA1, ACAT, ACC2, ADAMTS12, ADCY2, ADIPOQ, ADIPOR1, ADIPOR2, ADRB2, AGPAT5, AlP4, AKAP2, AKR1C2, AMPK, ANG2, ANK1, ANXA1, APOA1, ARHGAP17, ATP10A, AUH, AUTOTAXIN, BAI3, BCAR1, BIN1, BMP3A, CA10, CAMK1D, CAMKK2, CD36, CD44, CDC42, CDH13, CHAT, CNTFR, COL4A2, CPT, CSH1, CTNN, CUBN, CYP7B1, CYSLTR1, CYSLTR2, DGKB, DGKH, DGKZ, DHCR7, DHFR, DRD2, DRD5, EDG1, EDG2, EDG3, EDG4, EDG5, EDGE, EDG7, EDGE, EDNRA, EHHADH, ENPP6, ERBB4, ERK1, ERK2, ESRRG, ETFA, F2, FDPS, FGF2, FLNA, FLT4, FOXO1, FOXO3A, FTO, GABBR2, GATA3, GH1, GNA12, GNA13, GRK2, GRK5, GRM5, HAPLN1, HAS1, HAS2, HAS3, HCRTR2, HIF1A, HSD11B1, HYAL1, HYAL2, HYAL3, IL20RA, IL20RB, IL6ST, IL8, ITGA6, ITGB1, KDR, LAMA1, LDLR, LEPR, LEPTIN, LIFR, LIPL2, LKB1, LRP, LTBP2, MAT2B, ME1 MEGALIN, MERLIN, MET, MGST2, MMP2, MMP9, MTOR, MTR, NCK2, NEDD9, NFKB1, NFKBIB, NOS2A, NOS3, NR1I2, NR3C2, NRG1, NRP1, NRP2, OPRS1, OSBPL10, OSBPL3, OSTEOPONTIN, P2RY1, P2RY12, PAI1, PAI2, PAK1, PAK6, PALLD, PAP1, PAR1, PAXILLIN, PC, PCTP, PDE11A, PDE1A, PDE3A, PDE4D, PDE5, PDGFA, PDGFB, PDGFRA, PDGFRB, PI3K, PITPNC1, PKA, PKCD, PLA1A, PLA2, PLAT, PLAU, PLCB1, PLD1, PLD2, PLG, PLXDC2, PPARA, PPARG, PPARGC1B, PRKG1, PRL, PTGS2, PTN, PTPN11, PYK2, RAC1, RAS, RHEB, RHOA, ROCK1, ROCK2, RPS6KA1, RPS6 KB2, SCARB1, SCHIP1, SGPP2, SLC25A21, SMAD3, SMAD4, SNCA, SORBS2, SPLA2, SPOCK1, SRD5A1, SREBF1, SREBF2, STAT3, TGFBR1, TGFBR2, TGFBR3, THBS1, THBS2, THEM2, THRB, TIAM1, TIMP2, TLL2, TSC1, TSC2, TSPO, VEGFA, VEGFR1, and YES1.

The inventors have established that the above drugs and drug combinations provide improved and synergistic biological effect leading to an effective correction or normalization or functional dysregulation leading to AD and related disorders.

The above named compounds are listed in the following table 1, together with their CAS number. As discussed before, it should be understood that the invention encompasses the use of the above compounds as well as any pharmaceutically acceptable salt, hydrate, ester, ether, isomers, racemate, conjugates, or pro-drugs thereof. Prodrugs may be prepared (e.g., by coupling the drug to a suitable carrier) to offer a better control over the pharmacokinetic parameters of the treatment.

TABLE 1

| DRUG NAME | CAS NUMBER |
| --- | --- |
| Acamprosate | 77337-76-9 |
| Albuterol | 18559-94-9 |
| Alendronate | 66376-36-1 |
| Ambrisentan | 177036-94-1 |
| Aminocaproic acid | 60-32-2 |
| Argatroban | 74863-84-6 |
| Baclofen | 1134-47-0 |
| Balsalazide | 80573-04-2 |
| Becaplermin | 165101-51-9 |
| Cabergoline | 81409-90-7 |
| Cilostazol | 73963-72-1 |
| Clopidogrel | 113665-84-2 |
| Desirudin | 120993-53-5 |
| Dihydroergotamine | 6190-39-2 |
| Eplerenone | 107724-20-9 |
| Fenoldopam | 67227-57-0 |
| Fludrocortisone | 127-31-1 |
| Flunitrazepam | 1622-62-4 |
| Gemfibrozil | 25812-30-0 |
| Hesperetin | 520-33-2 |
| Imatinib | 152459-95-5 |
| Ketotifen | 34580-14-8 |
| Leflunomide | 75706-12-6 |
| Levosimendan | 141505-33-1 |
| L-histidine | 71-00-1 |
| Liothyronine - | 6893-02-3 |
| Marimastat | 154039-60-8 |
| Meloxicam | 71125-38-7 |
| Mepacrine | 83-89-6 |
| Methazolamide | 554-57-4 |
| Methimazole | 60-56-0 |
| Milrinone | 78415-72-2 |
| Montelukast | 158966-92-8 |
| Netilmicin | 56391-56-1 |
| Nitroglycerin | 55-63-0 |
| Nitroprusside | 15078-28-1 |
| Pegaptanib | 222716-86-1 |
| Pentazocine | 359-83-1 |
| Phenformin | 114-86-3 |
| Sodium phenylbutyrate | 1716-12-7 |
| Pyrimethamine | 58-14-0 |
| Sulfisoxazole | 127-69-5 |
| Sunitinib | 557795-19-4 |
| Tadalafil | 171596-29-5 |
| Temazepam | 846-50-4 |
| Terbinafine | 91161-71-6 |
| Thiethylperazine | 1420-55-9 |
| Tirofiban | 144494-65-5 |
| Topiramate | 97240-79-4 |
| Topotecan | 119413-54-6 |
| Vidarabine | 24356-66-9 |
| Warfarin | 81-81-2 |

Examples of pharmaceutically acceptable salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Additional examples of pharmaceutically acceptable inorganic or organic acid addition salts are listed in e.g., J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

Therapy according to the invention may be performed alone or as drug combination, and/or in conjunction with any other therapy, targeting the same pathway or having distinct modes of actions. It and may be provided at home, the doctor's office, a clinic, a hospital's outpatient department, or a hospital, so that the doctor can observe the therapy's effects closely and make any adjustments that are needed.

In a particular embodiment, the compositions of this invention further comprise at least one drug that modulates synapse function, preferably that ameliorates synapse function, for combined, separate or sequential use. More preferably, said at least one drug that modulates synapse function is selected from alfentanil, amiloride, amlodipine, aztreonam, buclizine, bumetanide, buprenorphine, lidocaine, chlorzoxazone, cinacalcet, dasatinib, dyphylline, eletriptan, ergotamine, fosphenyloin, phenobarbital, pregabalin, propylthiouracil, tiagabine, triamterene, vigabatrin and zonisamide (see table 2 below).

TABLE 2

| DRUG NAME | CAS NUMBER |
| --- | --- |
| Alfentanil | 71195-58-9 |
| Amiloride | 2016-88-8 |
| Amlodipine | 88150-42-9 |
| Aztreonam | 78110-38-0 |
| Buclizine | 82-95-1 |
| Bumetanide | 28395-03-1 |
| Buprenorphine | 52485-79-7 |
| Lidocaine | 137-58-6 |
| Chlorzoxazone | 95-25-0 |
| Cinacalcet | 226256-56-0 |
| Dasatinib | 302962-49-8 |
| Dyphylline | 479-18-5 |
| Eletriptan | 143322-58-1 |
| Ergotamine | 113-15-5 |
| Fosphenytoin | 93390-81-9 |
| Phenobarbital | 50-06-6 |
| Pregabalin | 148553-50-8 |
| Propylthiouracil | 51-52-5 |
| Tiagabine | 115103-54-3 |
| Triamterene | 396-01-0 |
| Vigabatrin | 60643-86-9 |
| Zonisamide | 68291-97-4 |

Alternatively, or in addition to the preceding embodiment, the compositions of this invention may further comprise at least one drug that modulates cell stress response, preferably that inhibits cell stress response, for combined, separate or sequential use. The most preferred drugs that modulate cell stress response are selected from arabitol, mannitol, metaraminol, omeprazole, prilocaine, rapamycin, rifabutin, thioguanine, trehalose and vidarabine (see table 3 below).

TABLE 3

| Drug name | CAS NUMBER |
| --- | --- |
| Arabitol | 488-82-4, 7643-75-6, 6018-27-5 |
| Mannitol | 69-65-8 |
| Metaraminol | 54-49-9 |
| Omeprazole | 73590-58-6 |
| Prilocaine | 721-50-6 |
| Rapamycin | 53123-88-9 |
| Rifabutin | 72559-06-9 |
| Thioguanine | 154-42-7 |
| Trehalose | 99-20-7 |
| Vidarabine | 24356-66-9 |

In a particular embodiment, the invention relates to a composition comprising a drug that increases angiogenesis, a drug that ameliorates synapse function, and a drug that inhibits cell stress response, for simultaneous, separate or sequential administration.

Other therapies used in conjunction with drug(s) or drug(s) combination(s) according to the present invention, may comprise one or more drug(s) that ameliorate symptoms of Alzheimer's disease or drug(s) that could be used for palliative treatment of Alzheimer's disease. Preferably, said one or more drug(s) is/are selected from 3APS, AAB-001, ABT-089, ABT-126, AC-3933, ACC-001, Acetaminophen, AFFITOPE AD01, AFFITOPE AD02, alpha-lipoic acid, alpha-tocopherol, AN1792, anti-Abeta, AQW051, Aripiprazole, Atomoxetine, Atorvastatin, AVE1625, AVP-923, AZD0328, AZD3480, Bapineuzumab, BAY94-9172 (ZK 6013443), Bifeprunox, Bioperine, BMS-708163, BRL-049653, Bryostatin, CAD106, Celecoxib, CERE-110, Cerebrolysin, CHF 5074, Choline, Circadin, Citalopram, Coenzyme Q, Copper, CTS21166, Curcumin, CX516 (Ampalex), CX717, Cyclophosphamate, DCB-AD1, Dextroamphetamine, DHA (Docosahexaenoic Acid), Digoxin, Dimebon (Latrepirdine), Divalproex, DMXB-A, Donepezil, Doxycycline, Egb 761, EHT 0202 tazolate, ELND005 (scyllo-inositol), EPAX 1050TG, Ergoloid mesylate, Epigallocatechin-Gallate, Escitalopram, Estradiol, Estrogen, Etanercept, EVP-6124, EVT101, Exelon, Fish oil, FK962, florpiramine F 18, Folate+Vitamin B6+Vitamin B21, Gabapentin, Galantamine, Gemfibrozil, *Ginkgo biloba* extracts (for example EGb 761 or CP401), improved extracts of *Ginkgo biloba* (for example enriched in active ingredients or lessened in contaminant) or drug containing *Ginkgo biloba* extracts (for example Tanakan or Gingkor fort), Glucose, L-Glutamic Acid, GSI 136, GSI-953, GSK239512, GSK933776A, Haloperidol, HF0220, Huperzine A, hydrocodone/APAP, Ibuprofen, IFN-alpha2A, Indomethacin, Insulin, Intravenous Immunoglobulin, Ketasyn, Lecozotan, Leuprolide, Levodopa, Lipoic Acid, Lithium, Lorazepam, Lovostatin, Lutein, LY2062430 (solanezumab), LY2811376, LY450139, LY451395, MABT5102A, Malate, Masitinib (AB1010), Medroxyprogesterone, Melatonin, MEM 1003, MEM 3454, Memantine, Methylene blue, Methylphenidate, Mifepristone, MK0249, MK0677, MK0952, MK0952, MK3328, Modafinil, MPC-7869, NADH, Naproxen, Nefiracetam, Neptune Krill Oil, Neramexane, NICS-15, Nicoderm Patch, Nicotinamide (vitamin B3), Novasoy, NPO31112, NS 2330, NSA-789, NSAIDs, Olanzapine, omega-3 polyunsaturated fatty acids (EPA+DHA), ONO-2506PO, Oxybate, *Panax Ginseng*, PAZ-417, PBT2, Perphenazine, PF-04360365, PF-04447943, PF-04494700, Phenserine, Phosphatidylserine, Pitavastatin, Posiphen, PPI-1019 (APAN), Pravastatin, Prazosin, Prednisone, Progesterone, PRX-03140, PYM50028, Quetiapine, R1450, Raloxifene, Ramipril, Rasagiline, Razadyne, resveratrol, rifampicin, risperidone, Rivastigmine, RN1219, R05313534, Rofecoxib, Rosiglitazone, *Salvia officinalis* (sage), SAM-315, SAM-531, SAM-760, SB-742457, Selenium, Sertraline, SGS-742, Simvastatin, SK-PC-B70M, Solanezumab, SR57667B, SRA-333, SRA-444, SSR180711c, ST101, T-817MA, Tacrine, Tarenflurbil, Testosterone, Tramiprosate (3APS), Trazodone, TRx0014 (methylthioninium chloride), Tryptophan, V950, Valproate, Varenicline, Vitamin C, Vitamin E, VP4896, Xaliproden, Zeaxanthin, Zolpidem, and ZT-1 (DEBIO-9902 SR).

The compositions of the invention typically comprise one or several pharmaceutically acceptable carriers or excipients. The duration of the therapy depends on the stage of the disease being treated, the combination used, the age and condition of the patient, and how the patient responds to the treatment.

The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recover from any as yet unforeseen side-effects. The drugs may also be formulated together such that one administration delivers all drugs.

The administration of each drug of the combination may be by any suitable means that results in a concentration of the drug that, combined with the other component, is able to correct the functioning of pathways implicated in AD.

While it is possible for the active ingredients of the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained in any appropriate amount in any suitable carrier substance, and is may be present in an amount of 1-99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Several drugs may be mixed together in the tablet, or may be partitioned. For example, the first drug is contained on the inside of the tablet, and the second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

Percutaneous and Topical Compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The Emulsifying Agents May be Naturally Occurring Gums (e.g., Gum Acacia or Gum Tragacanth)

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

Administration can be one to several times daily for several days to several years, and may even be for the life of the patient. Chronic or at least periodically repeated long-term administration will be indicated in most cases.

Additionally, pharmacogenomic (the effect of genotype on the pharmacokinetic, pharmacodynamic or efficacy profile of a therapeutic) information about a particular patient may affect the dosage used.

Except when responding to especially impairing AD disease cases when higher dosages may be required the preferred dosage of each drug in the combination usually lies within the range of doses not above those usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually no substantial effect. Accordingly, a particular advantage of the invention lies in the ability to use suboptimal doses of each compound, i.e., doses which are lower than therapeutic doses usually prescribed, preferably ½ of therapeutic doses, more preferably ⅓, ¼, ⅕, or even more preferably ¹⁄₁₀ to ¹⁄₁₀₀ of therapeutic doses. At such suboptimal dosages, the compounds alone would be substantially inactive, while the combination(s) according to the invention are fully effective.

A preferred dosage corresponds to amounts from 1% up to 50% of those usually prescribed for long-term maintenance treatment.

Specific examples of dosages are provided below:
Terbinafine orally from 2.5 to 75 mg per day,
Baclofen orally from 0.4 to 40 mg per day divided in two or three doses,
Phenformin orally from 0.5 to 25 mg per day,
Sulfisoxazole orally from 0.4 to 4 g per day divided in 4 to 6 doses.
Leflunomide orally from 0.25 to 12.5 mg per day,
Clopidogrel orally from 0.75 to 37.5 mg per day,
Mepacrine orally from 3 to 150 mg per day,
Phenformin orally from 0.5 to 25 mg per day.
The most preferred dosage corresponds to amounts from 1% up to 10% of those usually prescribed for long-term maintenance treatment. Examples of possible dosages for particular combination therapies of this invention are:
eplerenone orally from about 0.25 to 5 mg once or twice per day and marimastat orally from about 0.1 to 1 mg per day, gemfibrozil orally from about 12 to 120 mg administered in two divided doses 30 minutes before the morning and evening meal and marimastat orally from about 0.1 to 1 mg per day, marimastat orally from about 0.1 to 1 mg per day and terbinafine orally from about 2.5 to 25 mg once or twice daily topotecan orally from about 0.025 to 0.25 mg per day and methazolamide orally from about 1 to 10 mg 2-3 times daily eplerenone orally from about 0.25 to 5 mg once or twice per day and tadalafil orally from about 0.05 to 0.5 mg per day eplerenone orally from about 0.25 to 5 mg once or twice per day and cilostazol orally from about 1 to 10 mg per day, sunitinib orally from about 0.5 to 5 mg per day and terbinafine orally from about 2.5 to 25 mg once or twice daily, phenformin orally from about 0.5 to 5 mg per day and baclofen orally from about 0.4 to 8 mg per day administered in two or three divided doses, phenformin orally from about 0.5 to 5 mg per day and terbinafine orally from about 2.5 to 25 mg once or twice daily, tadalafil orally from about 0.05 to 0.5 mg per day, and alendronate orally from about 0.7 to 7 mg once weekly or 0.7 to 7 mg once once daily cilostazol orally from about 1 to 10 mg per day and alendronate orally from about 0.7 to 7 mg once weekly or 0.7 to 7 mg once once daily mepacrine orally from about 3 to 30 mg per day and terbinafine orally from about 2.5 to 25 mg once or twice daily, mepacrine orally from about 3 to 30 mg per day and balsalazide orally from about 7 to 75 mg to be taken 3 times a day terbinafine orally from about 2.5 to 25 mg once or twice daily and imatinib orally from about 4 to 60 mg per day It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

I. Compounds Prevent the Toxicity of $A\beta_{25-35}$ Peptide

In this first series of experiments, candidate compounds have been tested for their ability to prevent or reduce the toxic effects of $A\beta_{25-35}$ peptide.

Cell Culture:

Primo culture of rat endothelial cerebral cells (Vect-Horus SAS, Marseille) is cultivated on passage 0. At confluence, endothelial cells are dissociated with trypsin EDTA (Pan Biotech Ref: P10-023100). Cells are seeded at a density of 25 000 cells/well in 96 well-plates (wells are coated with 30 µl of type I rat collagen at 1.5 mg/ml, Vect-Horus SAS, Marseille) and are cultured in MCBD 131 medium (M-131-500, Invitrogen) supplemented with 1% of microvascular growth supplement (MVGS, S-005-25, Invitrogen). Cells are cultured at 37° C. in a humidified air (95%)/CO2(5%) atmosphere. Half of the medium is changed every other day with fresh medium. After 4 days, drugs are added to the cell culture medium, at different concentrations, solved in DMSO 0.1% or water. A 1 hour pre-incubation is performed, in a culture medium containing Dulbecco's modified Eagle's medium (DMEM, Pan Biotech Ref: P04-03600), supplemented with 2% of fetal bovine serum (FBS; Invitrogen ref: 16000-036), 1% of L-glutamine (Pan Biotech ref: P04-80100), 1% of Penicillin-Streptomycin (PS; Pan Biotech ref: P06-07100), 0.1 mg/ml of Heparin (Sigma), 10 ng/ml of epidermal growth factor (EGF, Invitrogen) and 10 ng/ml of vascular endothelial growth factor (VEGF, PHG0146, Invitrogen).

Cells are then intoxicated with 30 µM of β-amyloid (25-35; Sigma) together with drugs in the same culture medium. Cells are then intoxicated during 3 days.

Lactate Dehydrogenase (LDH) Activity Assay.

For each culture, after 3 days of intoxication, the supernatant is collected and analyzed with Cytotoxicity Detection Kit (LDH, Roche Applied Sciences). This colorimetric assay for the quantification of cell death is based on the measurement of lactate dehydrogenase (LDH) activity released from the cytosol of damaged cells into the supernatant. The optic density (DO) is assessed by spectrophotometer at 492 nm wavelength by a multiscan apparatus (Thermo, Ref Ascent).

Results

Figure 1:
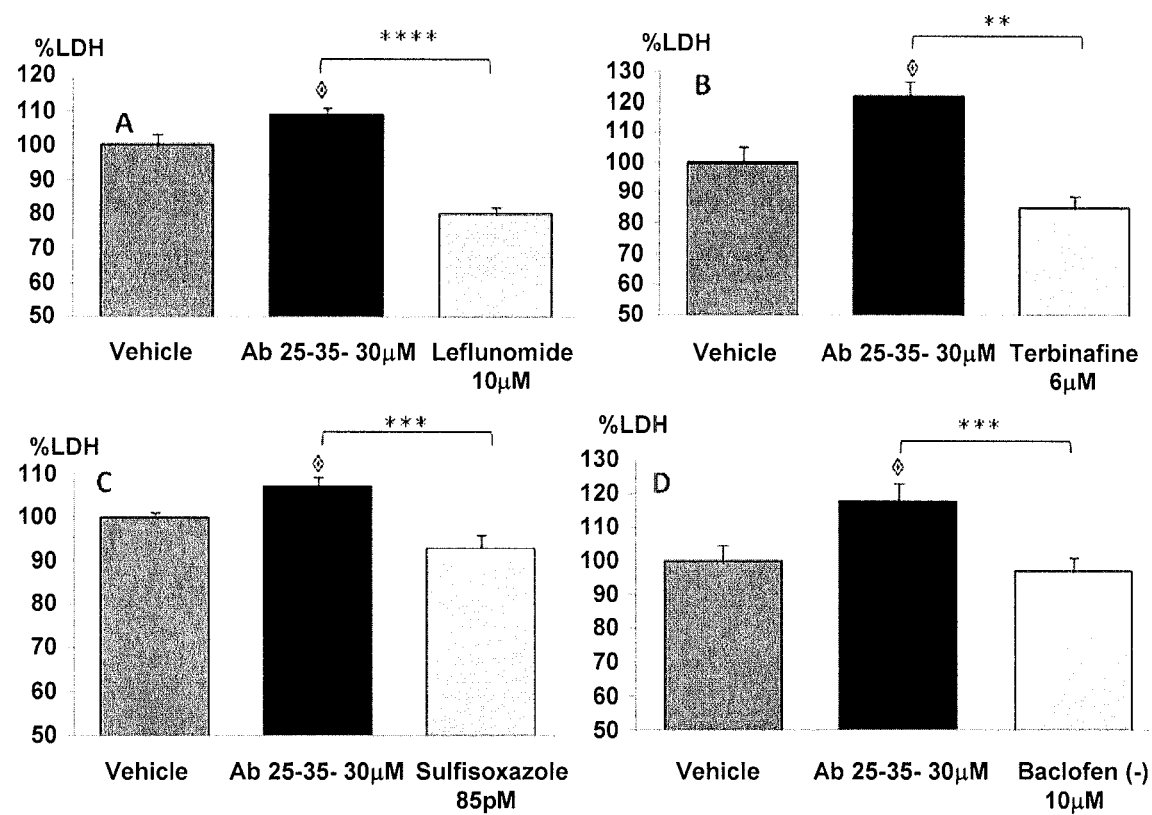
FIG. 1: Protective effect of selected drugs against beta-amyloid peptide toxicity on LDH release from rat endothelial cerebral cells. ◊: $p<0.05$: significantly different from vehicle. :$p<0.01$;*:$p<0.0001$; ****:$p<0.00001$: significantly different from A $\beta$25-35. Bilateral Student's t test. A $\beta_{25\text{-}35}$ 30 µM produces a moderate but significant intoxication (FIG. 1-A to D, in red). This intoxication is significantly prevented by Leflunomide (FIG. 1A), Terbinafine (FIG. 1B), Sulfisoxazole (FIG. 1C) or Baclofen (−) (FIG. 1D). Furthermore, Leflunomide and Terbinafine not only prevent amyloid deleterious effect, but also decrease spontaneous cell death in the culture medium.

Results presented in FIG. 1 are extracted from two independent cultures, 6 wells per condition. All values are expressed as mean±s.e.m. A bilateral Student's t test analysis is performed on raw data. Results are expressed in percentage of cell viability, compared to the control (vehicle).

Drugs are incubated with rat primary cerebral endothelial cells one hour before $A\beta_{25-35}$ 30 µM intoxication that lasts 3 days.

Three days after this incubation, LDH release in the culture medium is quantified, reflecting the level of cell death. The results clearly demonstrate a neuroprotective effect of the tested drugs of the invention against $A\beta_{25-35}$ intoxication (FIG. 1).

II. Compounds and Combinations Thereof Prevent the Toxicity of Human $A\beta_{1-42}$ Peptide In this further series of experiments, candidate compounds have been tested for their ability to prevent or reduce the toxic effects of human $A\beta_{1-42}$. $A\beta_{1-42}$ is the full length peptide that constitutes aggregates found in biopsies from human patients afflicted with AD. The drugs are first tested individually, followed by assays of their combinatorial action. The effect is determined on various cell types, to further document the activity of the compounds.

II.1. Protection Against the Toxicity of Human $A\beta_{1-42}$ Peptide in Rat Primary Cortical Neuron Cells Test Compound and Human Amyloid-β1-42 Treatment Primary rat cortical neurons are cultured as described previously.

Briefly, $A\beta_{1-42}$ peptide was reconstituted in define culture medium at 40 µM (mother solution) and was slowly shaked at +37° C. for 3 days in dark. The control medium was prepared in the same conditions.

After 3 days, the solution was used on primary cortical neurons as follows:

After 10 days of neuron culture, drug was solved in culture medium (+0.1% DMSO) and then pre-incubated with neurons for 1 hour before the $A\beta_{1-42}$ application (in a final volume per culture well of 100 µl). One hour after drug incubation, 100 µl of $A\beta_{1-42}$ peptide was added to a final concentration of 10 µM diluted in presence of drug, in order to avoid further drug dilutions. Cortical neurons were intoxicated for 24 hours. Three separate cultures were performed per condition, 6 wells per condition.

BDNF (50 ng/ml) and Estradiol-β (100 and 150 nM) were used as positive control and reference compounds respectively. Three separate cultures will be performed per condition, 12 wells per condition.

Organization of Culture Plates

Estradiol-β at 100 and 150 nM were used as reference test compound and BDNF at 50 ng/ml was used as a positive control.

Estradiol-β and BDNF were solved in culture medium and pre-incubated for 1 h before the amyloid-$\beta_{1-42}$ application.

The following conditions were assessed:
1 CONTROL PLAQUE: 12 wells/condition
  Negative Control: medium alone+0.1% DMSO
  Intoxication: amyloid-$\beta_{1-42}$ (10 µM) for 24 h
  Positive control: BDNF (50 ng/ml) 1 hr followed by amyloid-$\beta_{1-42}$ (10 µM) for 24 h
  Reference compound: Estradiol (150 nM) 1 hr followed by amyloid-$\beta_{1-42}$ (10 µM) for 24 h.
DRUG PLATE: 6 wells/condition
  Negative Control: medium alone+0.1% DMSO
  Intoxication: amyloid-$\beta_{1-42}$ (10 µM) for 24 h
  Drug 1: Drug 1-1 hr followed by amyloid-$\beta_{1-42}$(10 µM) for 24 h
  Drug 2: Drug 2-1 hr followed by amyloid-$\beta_{1-42}$(10 µM) for 24 h Lactate Dehydrogenase (LDH) Activity Assay 24 hours after intoxication, the supernatant was taken off and analyzed with Cytotoxicity Detection Kit (LDH, Roche Applied Science, ref: 11644793001, batch: 11800300). This colorimetric assay for the quantification of cell toxicity is based on the measurement of lactate dehydrogenase (LDH) activity released from the cytosol of dying cells into the supernatant.

Data Processing

All values are expressed as mean±s.e.mean of the 3 cultures (n=6 per condition). Statistic analyses were done on the different conditions (ANOVA followed by the Dunnett's test when it was allowed, Statviewi software version 5.0).

Results

Figure 3:
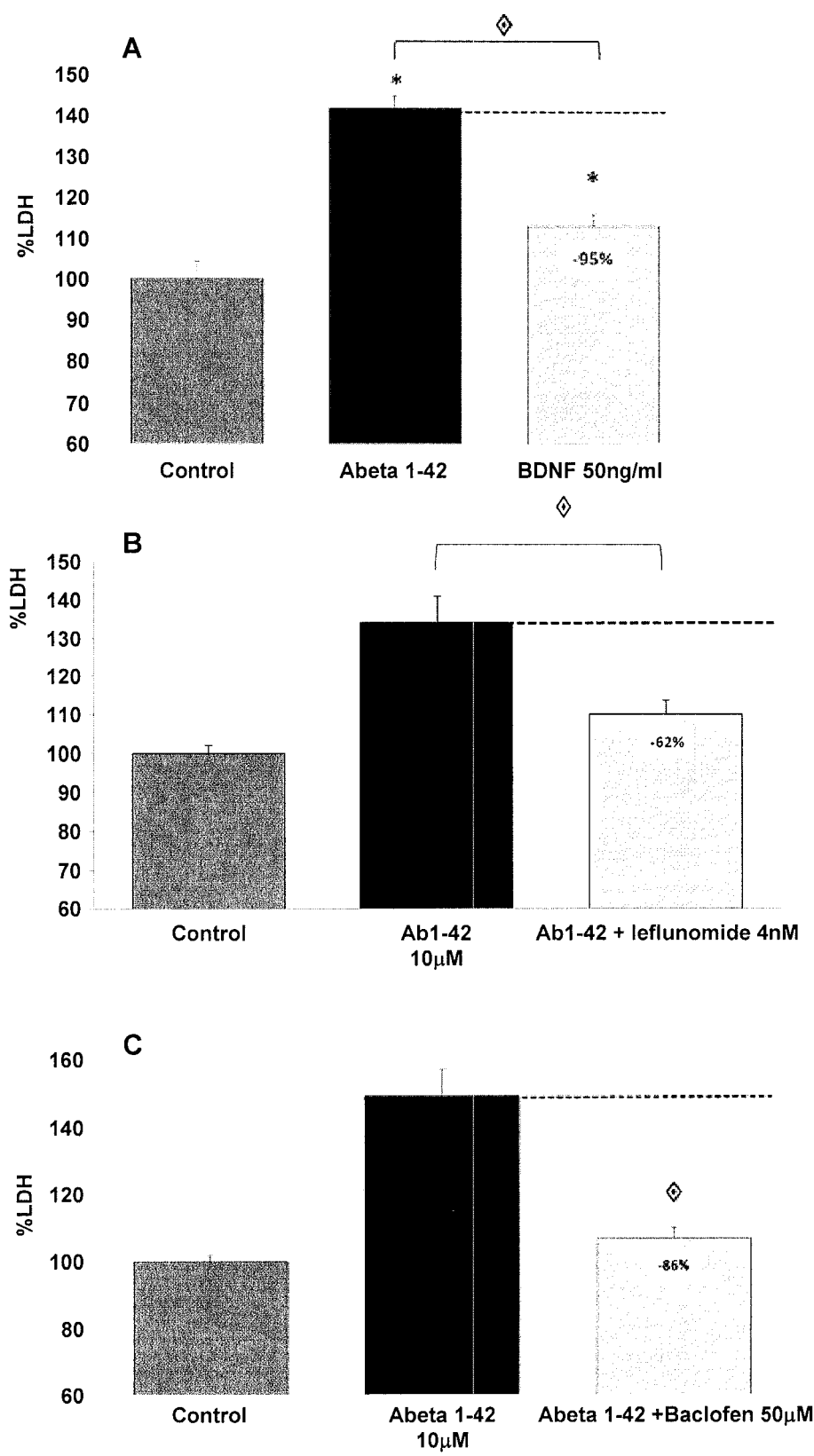
FIG. 3: Effect of selected drugs pretreatment on LDH release in human $A\beta_{1\text{-}42}$ toxicity on rat primary cortical cells. $A\beta_{1\text{-}42}$ produces a significant intoxication compared to vehicle-treated neurons. A) 1 hr of BDNF (50 ng/ml) pretreatment significantly protected the neurons from this amyloid injury (−95%), which is considered as a positive control for neuroprotection.*: $p<0.05$: significantly different from control (no intoxication); ◊: $p<0.05$: significantly different from Amyloid intoxication (ANOVA+Dunett Post-Hoc test). B) The intoxication is significantly prevented by leflunomide (−62%), ◊: $p<0.05$: significantly different from $A\beta_{1\text{-}42}$ intoxication (ANOVA+Dunett Post-Hoc test). $A\beta_{1\text{-}42}$ produces a significant intoxication compared to vehicle-treated neurons. C) The intoxication is significantly prevented by baclofen (−86%), ◊: $p<0.05$: significantly different from $A\beta_{1\text{-}42}$ intoxication (ANOVA+Dunett Post-Hoc test).

The results are presented in table 4 below and in FIG. 3. These results clearly demonstrate a substantive effect of the drugs of the invention on $A\beta_{1-42}$-intoxicated neural cells.

TABLE 4

| DRUG NAME | Protective effect on $A\beta_{1-42}$ toxicity in neuronal cells |
|---|---|
| Baclofen (+/−) | + |
| Leflunomide | + |
| Phenformin | + |
| Sulfisoxazole | + |

IL 2. Protection Against the Toxicity of Human $A\beta_{1-42}$ Peptide on Brain Microvascular Endothelial Cells Ultrastructural studies have shown that brain microvessels are closely associated with B-amyloid plaques, and that Alzheimer's disease brain capillaries contain preamyloid deposits (65). Damage to the vasculature resulting from Abeta deposition can result in a reduction of cerebral blood flow (66). Moreover, Abeta peptides have been shown to be potent inhibitors of angiogenesis in vitro and in vivo (64). Aβ1-42 is the full length peptide that constitutes aggregates found in biopsies from human patients that suffered from AD. To be the closest as possible of the human disease, the protection afforded by candidate compounds toward Aβ1-42 was assessed.

We therefore chose to use Human Brain Microvascular Endothelial Cells (HBMEC) to further illustrate the ability of the compounds to protect against the Aβ1-42 peptide injury. This model has been previously used to study the anti-angiogenic properties of mutant forms of Abeta peptide.

Human brain microvascular endothelial cerebral cells (HBMEC, ScienCell Ref: 1000, frozen at passage 10) were rapidly thawed in a waterbath at +37° C. The supernatant was immediately put in 9 ml Dulbecco's modified Eagle's medium (DMEM; Pan Biotech ref: PO4-03600) containing 10% of foetal calf serum (FCS; GIBCO ref 10270-106). Cell suspension was centrifuged at 180×g for 10 min at +4° C. and the pellets were suspended in CSC serum-free medium (CSC serum free, Cell System, Ref: SF-4Z0-500-R, Batch 51407-4) with 1.6% of Serum free RocketFuel (Cell System, Ref: SF-4Z0-500-R, Batch 54102), 2% of Penicillin 10.000 U/ml and Streptomycin 10 mg/ml (PS; Pan Biotech ref: PO6-07100 batch 133080808) and were seeded at the density of 20 000 cells per well in 96 well-plates (matrigel layer biocoat angiogenesis system, BD, Ref 354150, Batch A8662) in a final volume of 100 µl. On matrigel support, endothelial cerebral cells spontaneously started the process of capillary network morphogenesis (64).

Three separate cultures were performed per condition, 6 wells per condition.

Candidate Compounds and Human Amyloid-$\beta_{1-42}$ Treatment

Briefly, $A\beta_{1-42}$ peptide (Bachem, ref: H1368 batch 1010533) was reconstituted in define culture medium at 20 µM (mother solution) and was slowly shacked at +37° C. for 3 days in dark. The control medium was prepared in the same conditions.

After 3 days, this human amyloid peptide was used on HBMEC at 2.5 µM diluted in control medium (optimal incubation time). The $A\beta_{1-42}$ peptide was added 2 hours after HBMEC seeding on matrigel for 18 hours incubation.

One hour after HBMEC seeding on matrigel, test compounds and VEGF-165 were solved in culture medium (+0.1% DMSO) and then pre-incubated with HBMEC for 1 hour before the $A\beta_{1-42}$ application (in a final volume per culture well of 100 µl). One hour after test compounds or VEGF incubation (two hours after cell seeding on matrigel), 100 µl of $A\beta_{1-42}$ peptide was added to a final concentration of 2.5 µM diluted in control medium in presence of test compounds or VEGF (in a 200 µl total volume/well), in order to avoid further drug dilutions.

Organization of Culture Plates

VEGF-165, known to be a pro-angiogenic isoform of VEGF-A, was used for all experiments in this study as reference compound. VEGF-165 is one of the most abundant VEGF isoforms involved in angiogenesis. VEGF was used as reference test compound at 10 nM.

The following conditions were assessed:
Negative Control: medium alone+0.1% DMSO
Intoxication: amyloid-$\beta_{1-42}$ (2.5 µM) for 18 h
Positive control: VEGF-165 (10 nM) (1 reference compound/culture) 1 hr before the $A\beta_{1-42}$ (2.5 µM) addition for a 18 h incubation time.
Test compounds: Test compound 1 hr before the $A\beta_{1-42}$ (2.5 µM) addition for a 18 h incubation time.

Capillary Network Quantification

Per well, 2 pictures with 4× lens were taken using InCell Analyzer™ 1000 (GE Healthcare) in light transmission. All images were taken in the same conditions. Analysis of the angiogenesis networks was done using Developer software (GE Healthcare). The total length of capillary network was assessed.

Data Processing

All values are expressed as mean±s.e.mean of the 3 cultures (n=6 per condition). Statistic analyses were done on the different conditions performing an ANOVA followed by the Dunnett's test when it was allowed (Statview software version 5.0). The values (as %) inserted on the graphs show the amyloid toxicity evolution. Indeed, the amyloid toxicity was taken as the 100% and the test compound effect was calculated as a % of this amyloid toxicity.

Results

Figure 2:
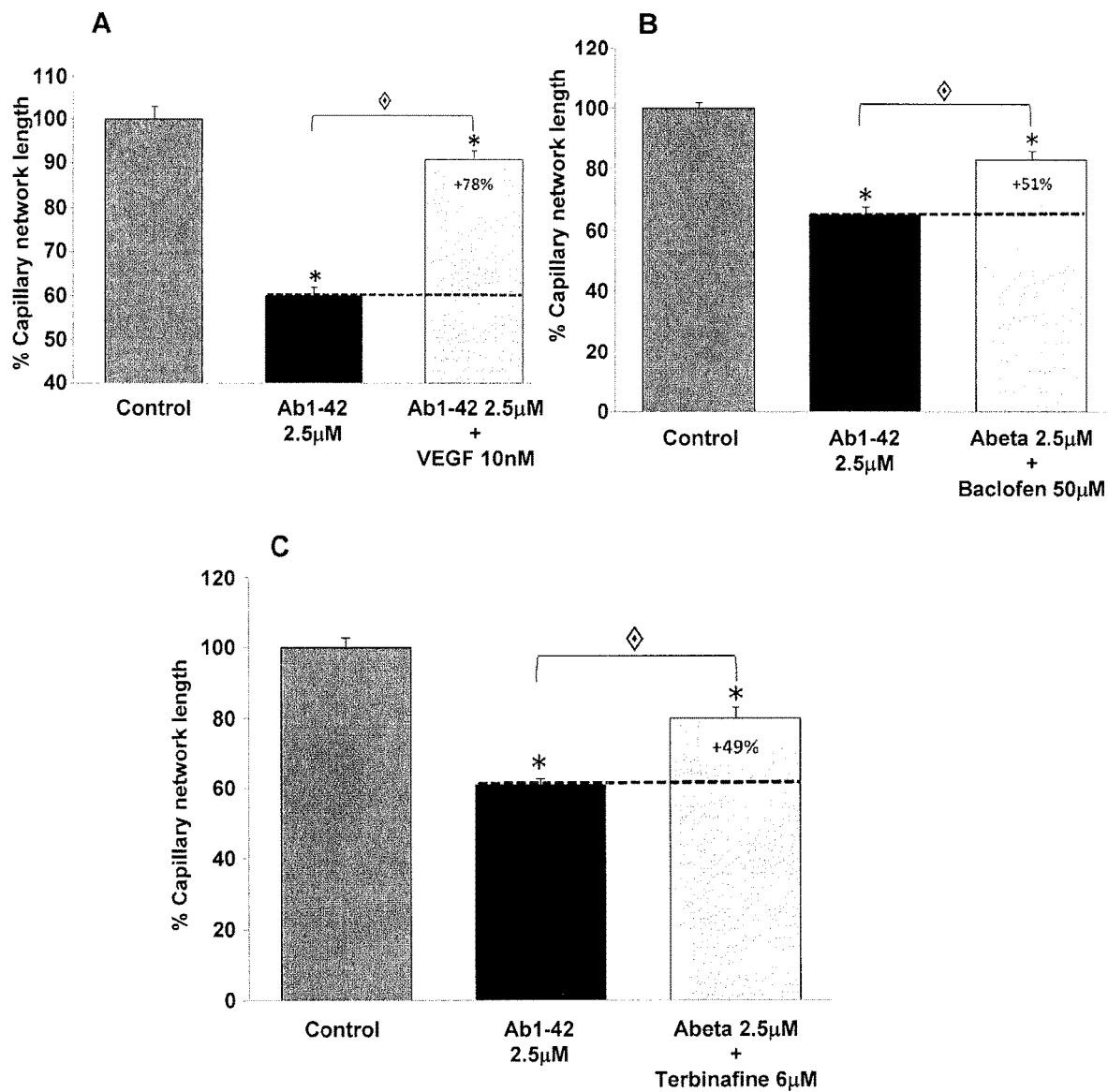
FIG. 2: Effect of selected drugs pretreatment against human $A\beta_{1\text{-}42}$ injury in HBMEC. (A) Validation of the experimental model used for drug screening: 1 hr of VEGF pre-treatment at 10 nM significantly protected the capillary network from this amyloid injury (+78% of capillary network compared to amyloid intoxication). *: $p<0.05$: significantly different from control (no intoxication) ◊: $p<0.05$: significantly different from Amyloid intoxication (ANOVA+Dunett Post-Hoc test). The intoxication is significantly prevented by Baclofen (2B) or Terbinafine (2C), ◊: $p<0.05$: significantly different from $A\beta_{1\text{-}42}$ intoxicated cells *: $p<0.05$: significantly different from control (ANOVA+Dunett Post-Hoc test).

Results are shown in FIG. 2 and in Table 5.

TABLE 5

| DRUG NAME | Protective effect in $A\beta_{1-42}$ intoxicated HBMC |
|---|---|
| Baclofen (+/−) | + |
| Fenoldopam | + |
| Sulfisoxazole | + |
| Levosimendan | + |
| Terbinafine | + |

These results clearly show a substantial protective effect of single drugs on human cells. These experiments also demonstrate a dose-response effect.

II.3. Effect of Combined Therapies on Toxicity of Human $A\beta_{1-42}$ Peptide on Human HBMEC Cells And in On Rat Primary Cortical Neuron Cells The inventors also confirmed the efficacy of drug combinations of the invention on human and rat cells. Protocols used in these experiments are the same as described in sections 1.2 and 1.3 above.

Results

The following drug combinations are tested on human brain microvascular endothelial cells and on rat primary cortical neuron cells:
baclofen and leflunomide,
terbinafine and sulfisoxazole,
terbinafine and leflunomide,
terbinafine and fenoldopam,
terbinafine and mepacrine,
terbinafine and phenformin,
terbinafine and clopidogrel,
baclofen and phenformin,
terbinafine and levosimendan,
baclofen and clopidogrel, or
baclofen and levosimendan.

All of the tested drug combinations give protective effect against toxicity of human $A\beta_{1-42}$ peptide in both models, as shown in Table 6 below.

TABLE 6

| DRUG NAME | Protective effect on $A\beta_{1-42}$ toxicity in neuronal cells | Protective effect in $A\beta_{1-42}$ intoxicated HBMEC cells |
|---|---|---|
| baclofen and leflunomide | + | + |
| terbinafine and sulfisoxazole | + | + |
| terbinafine and leflunomide | + | + |
| terbinafine and fenoldopam | + | + |
| terbinafine and mepacrine | + | + |
| terbinafine and phenformin | + | + |
| terbinafine and clopidogrel | + | + |
| baclofen and phenformin, | + | + |
| baclofen and clopidogrel | + | + |
| baclofen and levosimendan | + | + |
| levosimendan and terbinafine | + | + |

III. Terbinafine and Sulfisoxazole Combination Therapy Effectively Protects Neurons Against Toxicity of Human $A\beta_{1-42}$ In this example, combination therapy using Terbinafine and Sulfisoxazole was assessed for its ability to prevent or reduce the toxic effects of human $A\beta_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 4:
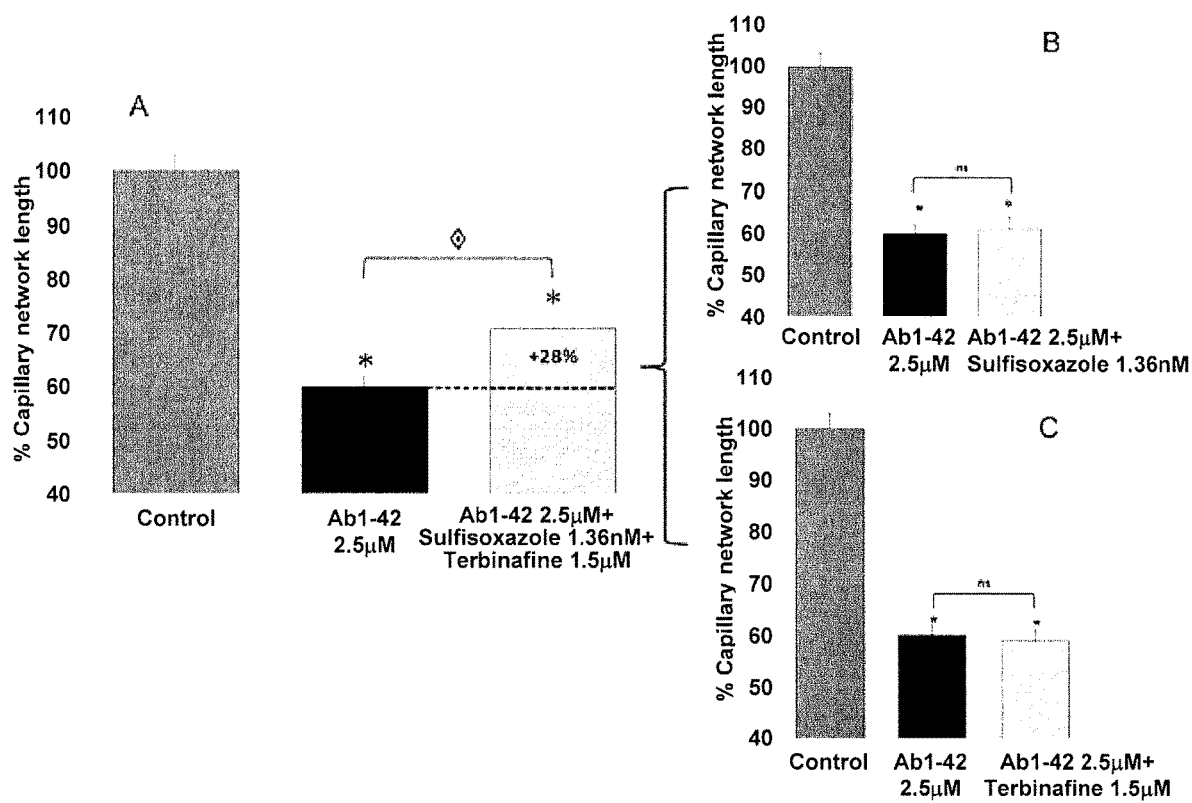
FIG. 4: Effect of a selected combination therapy on the total length of capillary network in beta-amyloid intoxicated HBMEC cultures. ◊: $p<0.05$: significantly different from $A\beta_{1\text{-}4}$. *: $p<0.05$: significantly different from vehicle$_2$. ANOVA+Bunett Post-Hoc test. The human amyloid peptide ($A\beta_{1\text{-}42}$ 2.5 µM) produces a significant intoxication, above 40%, compared to vehicle-treated neurons. This intoxication is significantly prevented by the combination of Sulfisoxazole and Terbinafine whereas, at these concentrations, Sulfisoxazole and Terbinafine alone have no significant effect on intoxication.

The results are presented FIG. 4. They clearly show that the aggregated human amyloid peptide ($A\beta_{1-42}$ 2.5 µM) produces a significant intoxication, above 40%, compared to vehicle-treated neurons. This intoxication is significantly prevented by the combination of Terbinafine and Sulfisoxazole (FIG. 4A) whereas, at those concentrations, Sulfisoxazole (FIG. 4B) and Terbinafine (FIG. 4C) alone have no significant effect on intoxication.

IV. Baclofen and Levosimendan Combination Therapy Effectively Protects Neurons Against Toxicity of Human $A\beta_{1-42}$ In this example, combination therapy using Baclofen and Levosimendan was assessed for its ability to prevent or reduce the toxic effects of human $A\beta_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 5:
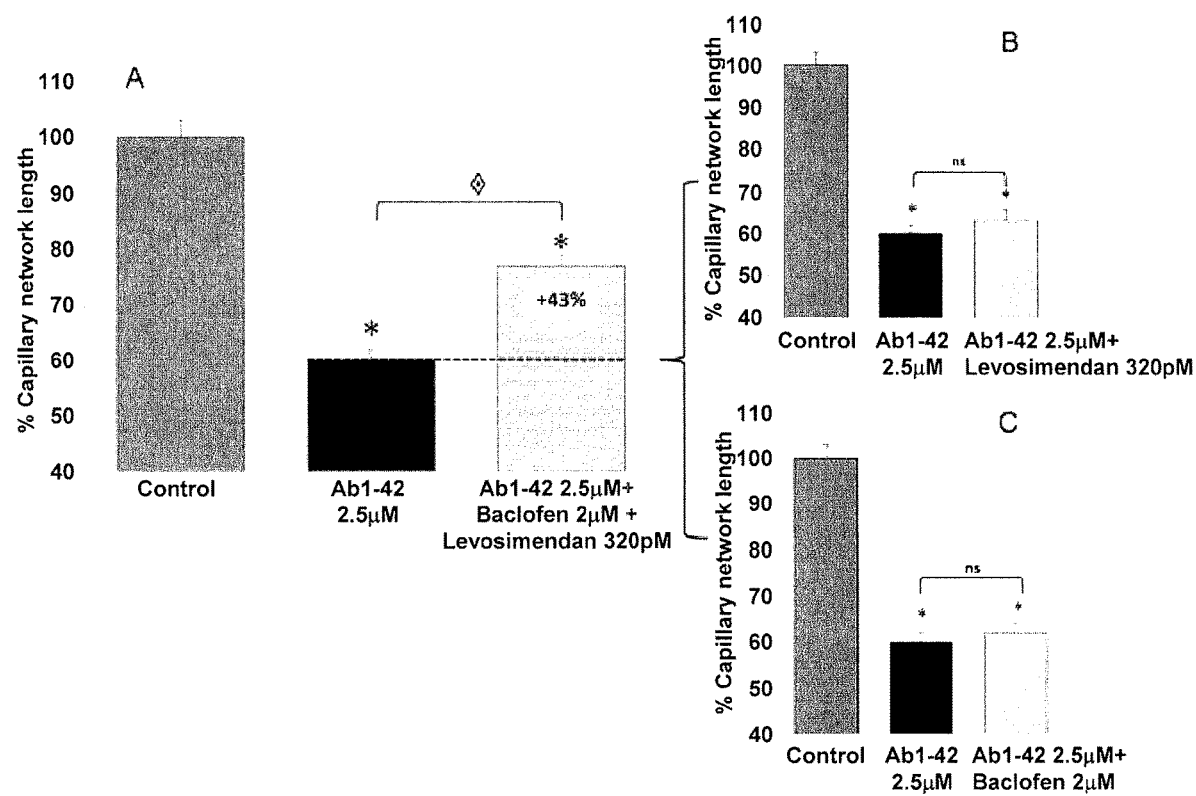
FIG. 5: Effect of a selected combination therapy on the total length of capillary network in beta-amyloid intoxicated HBMEC cultures. ◊: $p<0.05$, significantly different from $A\beta_{1\text{-}42}$. *: $p<0.05$, significantly different from vehicle.

The results are presented FIG. 5. They clearly show that the aggregated human amyloid peptide ($A\beta_{1-42}$ 2.5 µM) produces a significant intoxication, above 40%, compared to vehicle-treated neurons. This intoxication is significantly prevented by the combination of Baclofen and Levosimendan (FIG. 5A) whereas, at those concentrations, baclofen (FIG. 5B) and levosimendan (FIG. 5C) alone have no significant effect on intoxication.

V. Terbinafine and Levosimendan Combination Therapy Effectively Protects Neurons Against Toxicity of Human $A\beta_{1-42}$ In this example, combination therapy using Terbinafine and Levosimendan was assessed for its ability to prevent or reduce the toxic effects of human $A\beta_{1-42}$. The combination therapy was tested under experimental conditions disclosed in Example II.1. Human brain microvascular endothelial cell cultures were used, as disclosed in II. 1., and incubated simultaneously or sequentially with the drug combination.

The results are presented FIG. 6. They clearly show that the aggregated human amyloid peptide ($A\beta_{1-42}$ 2.5 µM) produces a significant intoxication, above 40%, compared to vehicle-treated neurons. This intoxication is significantly prevented by the combination of Terbinafine and Levosimendan (FIG. 6A) whereas, at those concentrations, terbinafine (FIG. 6B) and levosimendan (FIG. 6C) alone have no significant effect on intoxication.

VI. In Vivo Activity

Compounds and their combinations are tested in in vivo model of Alzheimer disease. Overexpression of Alzheimer's disease-linked mutant human amyloid beta protein precursor (APP) transgenes has been the most reliable means of promoting deposition of Abeta in the brains of transgenic mice that served as AD disease models in numerous studies. As they age, these mutant APP mice develop robust amyloid pathology and other AD-like features, including decreased synaptic density, reactive gliosis, and some cognitive deficits. Many mutant APP mouse models show little evidence of overt neuronal loss and neurofibrillary tangle (NFT) pathology. Mice hemizygous for this BRI-Abeta42 transgene are viable and fertile with a normal lifespan. Transgenic BRI-Abeta42 mRNA is expressed in a pattern characteristic of the mouse prion protein promoter; highest transgene expression levels are detected in the cerebellar granule cells and hippocampus, followed by the cortex, pons, thalamus, and midbrain. In the transgenic fusion protein, Abeta1-42 is fused to the C terminus of the BRI protein at the furin-like cleavage site such that cleavage results in efficient Abeta1-42 secretion into the lumen or extracellular space. Therefore, these mice specifically express the Abeta1-42 isoform. Hemizygous BRI-Abeta42 mice accumulate detergent-insoluble amyloid-beta with age and develop cored plaques in the cerebellum at as early as 3 months of age. Development of forebrain pathology occurs later, extracellular Abeta plaques are not present consistently in the hippocampus and entorhinal/piriform cortices until 12 months of age. Amyloid beta deposits (cored plaques) can be observed as early as 3 months in molecular layer of cerebella of transgenic mice and becoming more pronounced with age; occasional extracellular plaques are seen in the entorhinal/piriform cortices and hippocampus at 6 months of age, but aren't consistently found until >12 months of age. Oldest mice show widespread pathology with cored and diffuse plaques in cerebellum, cortex, hippocampus, and olfactory bulb. Extracellular amyloid plaques show dense amyloid cores with radiating fibrils; many bundles of dystrophic neurites are observed at the periphery of these plaques. Reactive gliosis is associated with plaques.

Drug Treatments

The transgenic Tg (Prnp-ITM2B/APP695*42) A12E mc mice (57) has been obtained from Jackson Laboratory (http://jaxmice.jax.org/strain/007002.html). Mice founder with the highest Abeta42 plasma levels, line BRI-Abeta42A (12e), have been maintained on a mixed B6C3 background. Adult male transgenic mice have free access to food and water. In accord with an approved the Institutional Animal Care and Use Committee protocol, mice have been weighed and injected i.p. or force fed once daily for 10 to 20 consecutive weeks with either a control solution (placebo) or PXT drugs, prepared at different doses.

Survival Analysis

Survival rates have been analyzed using Kaplan-Meier methods. Holm-Sidak methods (post hoc) have been used for all pairwise multiple comparison tests. The extraneous deaths are censored. All comparisons have been made between littermates to limit any potentially confounding effects from background strain differences.

Behavioural Tests

Behavioural tests were designed and conducted according to the methods published by several authors (58-61).

Spatial Learning and Memory in the Morris Water Maze (MWM)

This experiment is performed in a circular pool, 90 cm in diameter, made of white plastic and filled with milky colored water. An escape platform, 8 cm in diameter, made of clear plastic was submerged 0.5 cm under the water level. Visual clues are provided by different geometrical forms printed in A4-sized letters and placed on the four surrounding walls (distance from the pool was from 50 to 70 cm). Each mouse has been given four trials daily (5- to 7-minute interval between trials, a total of 16 trials) for 4 days. Each trial has been performed from one of four different starting points. The movement of the mice is monitored using Videotrack Software (View Point). The time taken to locate the escape platform (escape latency; up to 60 seconds) has been determined. After locating the platform the mouse has been allowed to sit on it for 15 seconds. Mice who failed to find the platform within 60 seconds have been guided to it and allowed to stay on it for 15 seconds. A latency of 60 seconds is entered into the record for such an occurrence. All four trials per day have been averaged for statistical analysis, except for the first trial on day 1. On day 9 (5 days after the last training) mice have been subjected to a 60-second probe trial in which the platform is removed and the mice are allowed to search for it. The time that each animal spent in each quadrant has been recorded (quadrant search time). Several groups of male mice have been used at 3, 7, 10, and 12 months.

The some few mice have showed freezing behaviour (eg, lying motionless in the water and refusing to swim) that strongly interfered with the test, these animals have been excluded from the data analysis.

All behavioural tests are conducted under a quiet and light-reduced environment.

Working Memory Test in Radial Arm Water Maze

This cognitive-based sensitive measure of working memory has been obtained with the help of the apparatus consisted of a 100 cm-diameter waterfilled pool (also used for the Morris water maze and Platform Recognition tasks) fitted with an aluminium insert to create six radially-distributed swim arms. Testing consists of five, 1-min trials per daily session, for 9-12 consecutive days. At the start of each session, a clear submerged platform is positioned at the end of one of the six swim arms (randomly-selected, changed daily). For each of the first four acquisition trials, the animal is placed into one of the non-platform containing arms (randomized sequence) and allowed to search for the platform. During the 60 s trial, each time the animal enters another non-platform containing arm, it is gently returned to its starting location and an error recorded. After the fourth trial, the animal is allowed to rest for 30 min, followed by a fifth (retention) trial, which originates in the final non-platform containing swim arm. The number of errors (incorrect arm choices) and escape latency (time to reach platform, maximum 60 s) are recorded for each trial.

Spatial Reference Learning and Memory in Circular Platform Test

This cognitive-based task test is performed with the help of the apparatus that consists of a 69 cm-diameter circular platform having 16 "escape" holes spaced equidistantly around the circumference. An escape refuge is installed beneath one of the holes, and a black curtain, on which are placed various visual cues, encircles the platform. The animal is placed in the center of the platform at the start of a single, 5 min trial and aversive stimuli (bright lights, fan wind) are presented. The total number of errors (head-pokes into non-escape holes) and escape latency (time to reach escape hole) are recorded.

Recognition Ability in Platform Recognition Test

This cognitive-based search task evaluates object identification and recognition ability. The target object consists of a 9 cm-diameter circular platform fitted with a 10 cm×40 cm black ensign, which is positioned 0.8 cm above the surface of the water in a 100 cm-diameter circular pool. Testing consists of four 60 s trials per day on each of four consecutive days. On each day, the target object is placed into a different quadrant of the pool for each trial, and the animal is released at the same location along the circumference of the pool for all four trials. The total latency (maximum 60 s) is recorded for each trial.

Modified Irwin Examination

A comprehensive screen, modified from Irwin is used to determine whether any of the mice exhibited physiological, behavioural, or sensorimotor impairments related to their genotype. To explore motor skills, coordination, and muscle strength, the mice are placed on a wire that was tightened between two 30-cm-high columns and their ability to balance on the wire is assessed. In addition, their ability to grasp and hang on the wire with all four paws for at least 5 seconds and to climb back on the wire is determined.

Quantification of Vascular Amyloid Deposition

For quantification of cerebral amyloid angiopathy (CAA), 5 µm paraffin-embedded sections at 30 µm intervals through the parietal or cerebellar cortex leptomeninges are immunostained with biotinylated-Ab9 antibody (anti-β1-16, 1:500) overnight at 4° C. (n=5-7 mice per genotype at each age group, n=6 sections per mouse). Positively stained blood vessels are visually assessed using modified Vonsattel's scoring system (62) The CAA severity score is calculated by multiplying the number of CAA vessels with the CAA severity grade.

Histology: Immunohistochemistry and Immunofluorescence

Tg and WT mice from 3 to 12 months are anesthetized and transcardially perfused sequentially with 0.9% NaCl and 4% paraformaldehyde in 0.1 mol/L phosphatebuffered saline (PBS) (pH 7.4) or 10% formalin and 4% paraformaldehyde in 0.1 mol/L PBS (pH 7.4). Brains and spinal cords are removed and stored in 4% paraformaldehyde. Some samples are embedded in paraffin and cut on a sliding microtome at a thickness of 10 µm. Cryosections (14 µm) are cut on a cryostat and mounted on chrome alum-coated slides. Endogenous peroxidase is quenched by treating the section with methanol containing 0.3% $H_2O_2$ for 30 minutes. Sections are blocked in 10% horse serum. Primary antibodies are used and incubated overnight at 4° C. in the presence of 1% horse serum. All secondary biotinylated or fluorescein-, Texas Red-, and AMCA-coupled antibodies, fluorochromes, ABC-kit, and 3,3'-diaminobenzidine as chromogen for peroxidase activity are from Vector Laboratories. Incubation with the secondary antibody is held at room temperature for 1 hour. All washing steps (3-10 minutes) and antibody dilution are performed using phosphate-buffered saline (0.1 mol/L PBS, pH 7.4) or Tris-buffered saline (0.01 mol/L Tris, 0.15 mol/L NaCl, pH 7.4). Incubation with the ABC complex and detection with 3,3'-diaminobenzidine is carried out according to the manufacturer's manual. Hematoxylin counterstaining is performed according to standard procedures. A minimum of three mice per genotype, age, and sex is used for each determination (63).

Statistical Analysis of in vivo Data.

Results from all experiments are analyzed with STATISTICA 8.0 (Statsoft). CAA severity are analyzed by using ANOVA with the post hoc Holm-Sidak multiple comparison test or two-tailed Student's t test. If the data set does not meet the parametric test assumptions, either the Kruskal-Wallis test followed by the post hoc Dunn's multiple comparison or the Mann-Whitney rank sum test is performed. All comparisons are made between littermates.

Drug response modelling is done excluding the control (0 mg/kg) samples. ED50 corresponds to the dose (mg/kg) required to induce a 50% of maximal drug-induced response in the experiments. It is calculated using the Hill equation model for the log of ED50.

In vivo experiments are performed for candidate drug combinations. Positive results on learning and spatial memory are listed in table 7 below.

TABLE 7

| Drug combination | Morris water Maze |
| --- | --- |
| Baclofen (+/−) and levosimendan | + |
| Sulfisoxazole and Terbinafine | + |
| Terbinafine and levosimendan | + |

BIBLIOGRAPHY

1. Crook R., Verkkoniemi A., et al. (1998). A variant of Alzheimer's disease with spastic paraparesis and unusual plaques due to deletion of exon 9 of presenilin 1. *Nat. Med.* 4(4): 452-5.
2. Houlden H., Baker M., et al. (2000). Variant Alzheimer's disease with spastic paraparesis and cotton wool plaques is caused by PS-1 mutations that lead to exceptionally high amyloid-beta concentrations. *Ann Neurol.* 48(5): 806-8.
3. Kwok J. B., Taddei K., et al. (1997). Two novel (M233T and R278T) presenilin-1 mutations in early-onset Alzheimer's disease pedigrees and preliminary evidence for association of presenilin-1 mutations with a novel phenotype. *Neuroreport.* 8(6): 1537-42.
4. Verkkoniemi A., Kalimo H., et al. (2001). Variant Alzheimer disease with spastic paraparesis: neuropathological phenotype. *J Neuropathol Exp Neurol.* 60(5): 483-92.
5. Citron M. (2004). Strategies for disease modification in Alzheimer's disease. Nat Rev *Neurosci.* 5(9): 677-85.
6. Suh Y. H. and Checker F. (2002). Amyloid precursor protein, presenilins, and alpha-synuclein: molecular pathogenesis and pharmacological applications in Alzheimer's disease. *Pharmacol Rev.* 54(3): 469-525.
7. Blacker D., Albert M. S., et al. (1994). Reliability and validity of NINCDS-ADRDA criteria for Alzheimer's disease. The National Institute of Mental Health Genetics Initiative. *Arch Neurol.* 51(12): 1198-204.

8. Rossor M. N., Fox N. C., et al. (1996). Clinical features of sporadic and familial Alzheimer's disease. *Neurodegeneration.* 5(4): 393-7.
9. Glenner G. G., Wong C. W., et al. (1984). The amyloid deposits in Alzheimer's disease: their nature and pathogenesis. *Appl Pathol.* 2(6): 357-69.
10. Ballatore C., Lee V. M., et al. (2007). Tau-mediated neurodegeneration in Alzheimer's disease and related disorders. *Nat Rev Neurosci.* 8(9): 663-72.
11. Bell K. F. and Claudio Cuello A. (2006). Altered synaptic function in Alzheimer's disease. *Eur J Pharmacol.* 545 (1): 11-21.
12. Hardy J. A. and Higgins G. A. (1992). Alzheimer's disease: the amyloid cascade hypothesis. *Science.* 256 (5054): 184-5.
13. Braak H. and Braak E. (1991). Neuropathological staging of Alzheimer-related changes. *Acta Neuropathol.* 82(4): 239-59.
14. Golde T. E. (2005). The Abeta hypothesis: leading us to rationally-designed therapeutic strategies for the treatment or prevention of Alzheimer disease. *Brain Pathol.* 15(1): 84-7.
15. Hardy J. and Selkoe D. J. (2002). The amyloid hypothesis of Alzheimer's disease: progress and problems on the road to therapeutics. *Science.* 297(5580): 353-6.
16. Selkoe D. J. (2000). The genetics and molecular pathology of Alzheimer's disease: roles of amyloid and the presenilins. *Neurol Clin.* 18(4): 903-22.
17. Patel N. S., Quadros A., et al. (2008). Potent anti-angiogenic motifs within the Alzheimer beta-amyloid peptide. *Amyloid.* 15(1):5-19.
18. Cai J., Jiang W. G., et al. (2006). Pigment epithelium-derived factor inhibits angiogenesis via regulated intracellular proteolysis of vascular endothelial growth factor receptor 1. *J Biol. Chem.* 281(6):3604-13.
19. Hainaud P., Contreras J. O., et al. (2006). The role of the vascular endothelial growth factor-Delta-like 4 ligand/Notch4-ephrin B2 cascade in tumor vessel remodeling and endothelial cell functions. *Cancer Res.* 66(17):8501-10.
20. Murakami D., Okamoto I., et al. (2003). Presenilin-dependent gamma-secretase activity mediates the intramembranous cleavage of CD44. *Oncogene.* 22(10): 1511-6.
21. West D. C., Hampson I. N., et al. (1985). Angiogenesis induced by degradation products of hyaluronic acid. *Science.* 228(4705): 1324-6.
22. Cao G., Savani R. C., et al. (2006). Involvement of endothelial CD44 during in vivo angiogenesis. *Am J Pathol.* 169(1): 325-36.
23. Sottile J. (2004). Regulation of angiogenesis by extracellular matrix. *Biochim Biophys Acta.* 1654(1): 13-22.
24. Hsieh M. Y., Chen W. Y., et al. (2006). Interleukin-20 promotes angiogenesis in a direct and indirect manner. *Genes Immun.* 7(3): 234-42.
25. Cao R., Brakenhielm E., et al. (2001). Leptin induces vascular permeability and synergistically stimulates angiogenesis with FGF-2 and VEGF. *Proc Natl Acad Sci USA.* 98(11): 6390-5.
26. Ferrara N., Gerber H. P., et al. (2003). The biology of VEGF and its receptors. *Nat. Med.* 9(6): 669-76.
27. Ge G., Fernandez C. A., et al. (2007). Bone morphogenetic protein 1 processes prolactin to a 17-kDa antiangiogenic factor. *Proc Natl Acad Sci USA.* 104(24):10010-5.
28. Hardie D. G. (2007). AMP-activated/SNF1 protein kinases: conserved guardians of cellular energy. *Nat Rev Mol Cell Biol.* 8(10): 774-85.
29. Nagata D., Mogi M., et al. (2003). AMP-activated protein kinase (AMPK) signaling in endothelial cells is essential for angiogenesis in response to hypoxic stress. *J Biol. Chem.* 278(33):31000-6.
30. Reihill J. A., Ewart M. A., et al. (2007). AMP-activated protein kinase mediates VEGF-stimulated endothelial NO production. *Biochem Biophys Res Commun.* 354(4):1084-8.
31. Ouchi N., Kobayashi H., et al. (2004). Adiponectin stimulates angiogenesis by promoting cross-talk between AMP-activated protein kinase and Akt signaling in endothelial cells. *J Biol. Chem.* 279(2):1304-9.
32. Lopez-Lopez C., Dietrich M. O., et al. (2007). Disturbed cross talk between insulin-like growth factor I and AMP-activated protein kinase as a possible cause of vascular dysfunction in the amyloid precursor protein/presenilin 2 mouse model of Alzheimer's disease. *J Neurosci.* 27(4): 824-31.
33. Hug C., Wang J., et al. (2004). T-cadherin is a receptor for hexameric and high-molecular-weight forms of Acrp30/adiponectin. *Proc Natl Acad Sci USA.* 101(28): 10308-13.
34. Feksa L. R., Cornelio A. R., et al. (2003). Characterization of the inhibition of pyruvate kinase caused by phenylalanine and phenylpyruvate in rat brain cortex. *Brain Res.* 968(2): 199-205.
35. Feksa L. R., Cornelio A. R., et al. (2003). Alanine prevents the inhibition of pyruvate kinase activity caused by tryptophan in cerebral cortex of rats. *Metab Brain Dis.* 18(2): 129-37.
36. Hardie D. G. and Frenguelli B. G. (2007). A neural protection racket: AMPK and the GABA(B) receptor. *Neuron.* 53(2): 159-62.
37. Oikari S., Ahtialansaari T., et al. (2008). Downregulation of PPARs and SREBP by acyl-CoA-binding protein overexpression in transgenic rats. *Pflugers Arch.* 456(2):369-77.
38. Morfin R. and Stárka L. (2001). Neurosteroid 7-hydroxylation products in the brain. *International review of neurobiology.* 46(79-95.
39. Hirsch-Reinshagen V., Zhou S., et al. (2004). Deficiency of ABCA1 impairs apolipoprotein E metabolism in brain. *J Biol. Chem.* 279(39): 41197-207.
40. English D., Kovala A. T., et al. (1999). Induction of endothelial cell chemotaxis by sphingosine 1-phosphate and stabilization of endothelial monolayer barrier function by lysophosphatidic acid, potential mediators of hematopoietic angiogenesis. *J Hematother Stem Cell Res.* 8(6):627-34.
41. Park S. Y., Jeong K. J., et al. (2007). Hypoxia enhances LPA-induced HIF-1alpha and VEGF expression: their inhibition by resveratrol. *Cancer Lett.* 258(1):63-9.
42. Tsopanoglou N. E., Pipili-Synetos E., et al. (1994). Leukotrienes C4 and D4 promote angiogenesis via a receptor-mediated interaction. *Eur J Pharmacol.* 258(1-2): 151-4.
43. Hoang M. V., Whelan M. C., et al. (2004). Rho activity critically and selectively regulates endothelial cell organization during angiogenesis. *Proc Natl Acad Sci USA.* 101(7): 1874-9.
44. Kanayasu T., Nakao-Hayashi J., et al. (1989). Leukotriene C4 stimulates angiogenesis in bovine carotid artery endothelial cells in vitro. *Biochem Biophys Res Commun.* 159(2): 572-8.
45. Lee O. H., Kim Y. M., et al. (1999). Sphingosine 1-phosphate induces angiogenesis: its angiogenic action and signaling mechanism in human umbilical vein endothelial cells. *Biochem Biophys Res Commun.* 264(3): 743-50.
46. Fukushima N., Weiner J. A., et al. (2002). Lysophosphatidic acid influences the morphology and motility of young, postmitotic cortical neurons. *Mol Cell Neurosci.* 20(2):271-82.
47. van Meeteren L. A., Ruurs P., et al. (2006). Autotaxin, a secreted lysophospholipase D, is essential for blood vessel formation during development. *Mol Cell Biol.* 26(13): 5015-22.
48. Buhl A. M., Johnson N. L., et al. (1995). G alpha 12 and G alpha 13 stimulate Rho-dependent stress fiber formation and focal adhesion assembly. *J Biol. Chem.* 270(42): 24631-4.
49. Umemura K., Yamashita N., et al. (2006). Autotaxin expression is enhanced in frontal cortex of Alzheimer-type dementia patients. *Neurosci Lett.* 400(1-2): 97-100.
50. Sayas C. L., Moreno-Flores M. T., et al. (1999). The neurite retraction induced by lysophosphatidic acid increases Alzheimer's disease-like Tau phosphorylation. *J Biol. Chem.* 274(52):37046-52.
51. Stein T. D. and Johnson J. A. (2002). Lack of neurodegeneration in transgenic mice overexpressing mutant amyloid precursor protein is associated with increased levels of transthyretin and the activation of cell survival pathways. *J Neurosci.* 22(17):7380-8.
52. Beglopoulos V., Sun X., et al. (2004). Reduced beta-amyloid production and increased inflammatory responses in presenilin conditional knock-out mice. *J Biol. Chem.* 279(45):46907-14.
53. Regland B. and Gottfries C. G. (1992). Slowed synthesis of DNA and methionine is a pathogenetic mechanism common to dementia in Down's syndrome, AIDS and Alzheimer's disease? *Med. Hypotheses.* 38(1): 11-9.
54. Coma M. et al. (2005) Lack of oestrogen protection in amyloid-mediated endothelial damage due to protein nitrotyrosination. Brain 128:1613-1621.
55. Mosmann T. (1983) Rapid colorimetric assay for cellular growth and survival: application to proliferation and cytotoxicity assays. J Immunological Methods 65:55-63.
56. P. J. Mitchell et al. (2007) A quantitative method for analysis of in vitro neurite outgrowth. Journal of Neuroscience Methods 164 350-362
57. McGowan E., et al. (2005) Aβ42 Is Essential for Parenchymal and Vascular Amyloid Deposition in Mice. Neuron 47: 191-199.
58. Leighty R. E. et al. (2008) Use of artificial neural networks to determine cognitive impairment and therapeutic effectiveness in Alzheimer's transgenic mice. Journal of Neuroscience Methods 167: 358-366
59. Ashe K H (2001) Learning and memory in transgenic mice modelling Alzheimer's disease. Learning and Memory 8: 301-308.
60. Carlson G A, et al. (1997) Genetic modification of the phenotypes produced by amyloid precursor protein overexpression in transgenic mice. Human Molecular Genetics 6:1951-1959.
61. Hsiao K, et al. (1996) Correlative memory deficits, Abeta elevation, and amyloid plaques in transgenic mice. Science 274: 99-102.
62. Greenberg S. M. and Vonsattel J. P. (1997) Diagnosis of cerebral amyloid angiopathy. Sensitivity and specificity of cortical biopsy. Stroke 28(7):1418-22
63. Schindowski K. et al. (2006) Alzheimer's Disease-Like Tau Neuropathology Leads to Memory Deficits and Loss of Functional Synapses in a Novel Mutated Tau Transgenic Mouse without Any Motor Deficits. Am J. Pathol. 169: 599-616.
64. Paris D, et al. (2005) Anti-angiogenic activity of the mutant Dutch A(beta) peptide on human brain microvascular endothelial cells. *Brain Res Mol Brain Res.* 136: 212-30.
65. Miyakawa T (1997) Electron microscopy of amyloid fibrils and microvessels. *Ann NY Acad Sci* 826: 25-34.
66. Smith E E, et al (2009) Beta-amyloid, blood vessels, and brain function. Stroke. 40: 2601-6.

The invention claimed is:

1. A method for treating Alzheimer's disease in a subject suffering from Alzheimer's disease, the method comprising the chronic administration to the subject in need thereof of an effective amount of baclofen, a salt of baclofen, or a sustained release formulation of said baclofen or salt of baclofen, wherein the baclofen is chronically administered orally at a dose of 0.4 mg to 40 mg per day.

2. The method of claim 1, wherein the daily dose of baclofen is administered in two or three doses.

3. The method of claim 1, further comprising simultaneously, separately, or sequentially administering to the subject at least one additional compound chosen from the group consisting of sulfisoxazole, clopidogrel, fenoldopam, mepacrine, levosimendan, and phenformin, or a salt of said additional compound, or a sustained release formulation of said additional compound or salt thereof.

4. The method of claim 3, wherein the subject is administered with baclofen and levosimendan, baclofen and sulfisoxazole, baclofen and phenformin, or baclofen and clopidogrel, wherein said baclofen, levosimendan, sulfisoxazole, phenformin and clopidogrel may be in the form of a salt thereof or in the form of a sustained release formulation of said baclofen, levosimendan, sulfisoxazole, phenformin, or clopidogrel or salt thereof.

5. A method for protecting endothelial or neuronal cells against the toxicity of Abeta peptide in a subject having Alzheimer's disease, comprising the chronic administration to said subject (i) baclofen or terbinafine, or (ii) a salt of baclofen or terbinafine, or (iii) a sustained release formulation of said baclofen or terbinafine or salt thereof, wherein the baclofen or terbinafine is chronically administered orally at a dose of 0.4 mg to 40 mg per day.

6. A method for retardation or reduction of symptoms of Alzheimer's disease in a subject suffering from Alzheimer's disease, the method comprising the chronic administration to the subject in need thereof of an effective amount of baclofen, a salt of baclofen or a sustained release formulation of said baclofen or salt thereof, wherein the baclofen is chronically administered orally at a dose of 0.4 mg to 40 mg per day.

7. The method of claim 5, wherein the daily dose of baclofen is administered in two or three doses.

8. The method of claim 5, further comprising simultaneously, separately, or sequentially administering to the subject at least one additional compound chosen from the group consisting of sulfisoxazole, clopidogrel, fenoldopam, mepacrine, levosimendan, and phenformin, or a salt of said additional compound, or a sustained release formulation of said additional compound or salt thereof.

9. The method of claim 8, wherein the subject is administered with baclofen and levosimendan, baclofen and sulfisoxazole, baclofen and phenformin, or baclofen and clopidogrel, wherein said baclofen, levosimendan, sulfisoxazole, phenformin and clopidogrel may be in the form of a salt thereof or in the form of a sustained release formulation of said baclofen, levosimendan, sulfisoxazole, phenformin, or clopidogrel or salt thereof.

10. The method of claim 6, wherein the daily dose of baclofen is administered in two or three doses.

11. The method of claim 6, further comprising simultaneously, separately, or sequentially administering to the subject at least one additional compound chosen from the group consisting of sulfisoxazole, clopidogrel, fenoldopam, mepacrine, levosimendan, and phenformin, or a salt of said additional compound, or a sustained release formulation of said additional compound or salt thereof.

12. The method of claim 11, wherein the subject is administered with baclofen and levosimendan, baclofen and sulfisoxazole, baclofen and phenformin, or baclofen and clopidogrel, wherein said baclofen, levosimendan, sulfisoxazole, phenformin and clopidogrel may be in the form of a salt thereof or in the form of a sustained release formulation of said baclofen, levosimendan, sulfisoxazole, phenformin, or clopidogrel or salt thereof.

* * * * *